(12) United States Patent
Bezwada

(10) Patent No.: US 7,691,364 B2
(45) Date of Patent: *Apr. 6, 2010

(54) FUNCTIONALIZED DRUGS AND POLYMERS DERIVED THEREFROM

(75) Inventor: Rao S. Bezwada, Whitehouse Station, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 870 days.

This patent is subject to a terminal disclaimer.

(21) Appl. No.: 11/233,876

(22) Filed: Sep. 23, 2005

(65) Prior Publication Data

US 2006/0172983 A1 Aug. 3, 2006

Related U.S. Application Data

(60) Provisional application No. 60/647,996, filed on Jan. 28, 2005.

(51) Int. Cl.
*A61K 31/74* (2006.01)
(52) U.S. Cl. .................................................. 424/78.08
(58) Field of Classification Search ........................ None
See application file for complete search history.

(56) References Cited

U.S. PATENT DOCUMENTS 4,938,949 A 7/1990 Borch et al. .................. 424/10

OTHER PUBLICATIONS

Wang et al, Chinese Journal of Inorganic Chemistry Jul. 2004.*
Heylin in Chemical and Engineering News, Jul. 24, 2006.*

NCI Clinical Trials PDQ, downloaded from the world wide web at http://www.cancer.gov/clinicaltrials/CINJ-040412 on Dec. 6, 2008.*

* cited by examiner

*Primary Examiner*—Eric E. Silverman
(74) *Attorney, Agent, or Firm*—Fox Rothschild LLP

(57) ABSTRACT

Compounds selected from:

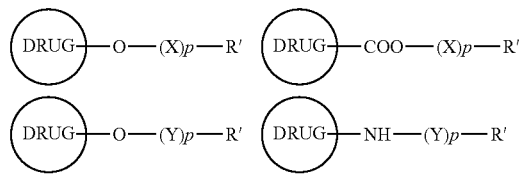

where DRUG-OH, DRUG-COOH and DRUG-$NH_2$ are biologically active compounds; each X is independently selected from —$CH_2COO$-(glycolic acid moiety), —$CH(CH_3)COO$-(lactic acid moiety), —$CH_2CH_2OCH_2COO$-(dioxanone moiety), —$CH_2CH_2CH_2CH_2CH_2COO$-(caprolactone moiety), —$(CH_2)_yCOO$—, where y is 2-4 or 6-24 and —$(CH_2CH_2O)_zCH_2COO$—, where z is 2-24; each Y is independently selected from —$COCH_2O$-(glycolic ester moiety), —$COCH(CH_3)O$-(lactic ester moiety), —$COCH_2OCH_2CH_2O$-(dioxanone ester moiety), —$COCH_2CH_2CH_2CH_2CH_2O$-(caprolactone ester moiety), —$CO(CH_2)_mO$—, where m is 2-4 or 6-24 and —$COCH_2O(CH_2CH_2O)_n$-where n is between 2-24; R' is hydrogen, benzyl or an alkyl group, the alkyl group being either straight-chained or branched; and p is 1-6. Multi-functional compounds and drug dimers, oligomers and polymers are also disclosed.

11 Claims, No Drawings

FUNCTIONALIZED DRUGS AND POLYMERS DERIVED THEREFROM

CROSS-REFERENCE TO RELATED APPLICATIONS

The present application claims priority benefit under 35 U.S.C. §119(e) of U.S. Provisional Patent Application Ser. No. 60/647,996 filed Jan. 28, 2005 and under 35 U.S.C. §120 as a Continuation-In Part of U.S. patent application Ser. No. 11/220,044 filed Sep. 6, 2005. The disclosures of both applications are incorporated herein by reference.

BACKGROUND OF THE INVENTION

The present invention relates to functionalized drugs and their polymers with controllable degradation profiles, releasing the active component over a desired time range.

The drugs in the context of the present invention are defined chemically as a biologically active substance which has one or more aromatic rings and bears one or more hydroxyl, amino or carboxylic acid substituents on the ring, including functional derivatives such as esters, amides, methyl ethers, glycosides and other derivatives that are apparent to those skilled in the art. Phenol (hydroxybenzene) is the simplest example of a phenolic compound, but most phenolics have two or more hydroxyl groups and are bioactive substances occurring widely in food plants that are eaten regularly by substantial numbers of animals and people and have been found to be safe compounds. Included in the definition of biologically active phenolics are poly-phenols having complex substitution patterns and compounds having condensed rings.

Examples of naturally occurring biologically active phenolics include, but are not limited to: bergaptol, caffeic acid, capsaicin, coumarin, daidzein, 2,5-dihydroxy-benzoic acid, ferulic acid, flavonoids, glycitein (isoflavone), 4-hydroxycinnamic acid, 4-hydroxy-coumarin, isopimpinellin, resveratrol, synapic acid, vanillic acid, vanillin, and the derivatives of all of the above.

Capsaicin is a biologically active phenolic that is the active component of cayenne pepper. The capsaicins are amides of vanillylamine and $C_8$ to $C_{13}$ branched fatty acids. Topical application of capsaicin stimulates and blocks small pain fibers by depleting them of the neurotransmitter substance P that mediates pain impulses. A cream made from 0.025%-0.075% capsaicin applied 4× daily may help peripheral neuropathic pain, post-herpetic neuralgia, trigeminal neuralgia, psoriasis and fibromyalgia. It is also useful for diabetic neuropathy, cluster headaches, earache, osteo- and rheumatoid arthritis. Capsaicin is a powerful pain reliever.

Naproxen, paracetanol, acetaminophen and acetylsalicylic acid are biologically active phenolics that belong to the class of drugs called non-steroidal anti-inflammatory drugs or NSAIDs. The NSAIDs provide relief by blocking the action of prosta-glandins, which are hormone-like substances that contribute to pain, inflammation, fever and muscle cramps.

Phenolic moieties, synthetic and naturally occurring, are part of many drugs. Examples of these medicinals include acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, bupheniode, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochloride, ketobemidone, khellin, labetalol, lactylphenetidin, levodopa. levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, nonnolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, α-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

Other bioactive phenolics include acacetin, 4-acetamido-2-methyl-1-naphthol, acetaminophen, albuterol, allenolic acid, aloe emodin, aloin, β-amino-4-hydroxy-3,5-diiodohydrocinnamic acid, N-(5-amino-2-hydroxyphenyl)-benzeneacetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, aspirin, baptigenin, benzestrol, benzoresorcinol, bisphenol a, bisphenol b, butylated hydroxylanisole, butylated hydroxytoluene, capobenic acid, trans-1-(3'-carboxy-4'-hydroxyphenyl)-2-(2",5"-dihydroxyphenyl)ethane, catechin, chlorogenic acid, m-chlorophenol, 5-chloro-8-quinolinol, chloroxylenol, chlorquinaldol, chromonar, chrysin, cinametic acid, clorophene, coniferyl alcohol, p-coumaric acid, coumestrol, coumetarol, daphnetin, datiscetin, deoxyepinephrine, 3,5-diiodothyronine, 3,5-diiodotyrosine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, ferulic acid, fisetin, 3-fluoro-4-hydroxyphenylacetic acid, fraxetin, fustin, galangin, gallacetophenone, gallic acid, gardenins, genistein, gentisyl alcohol, gepefrine, geranylhydroquinone, [6]-gingerol, gossypol, guaiacol, guaifenesin, harmalol, hematoxylin, hinderin, homoeriodictyol, homogentisic acid, homovanillic acid, hydroxyamphetamine, 2-hydroxy-5-(2,5-dihydroxybenzylamino)-2-hydroxybenzoic acid, 4-hydroxy-3-methoxy-mandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxyphenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl)methylenepropanedinitrile, thymol, thyropropic acid, thyroxine, tiratricol, tyrosine, vanillic acid, vanillin.

Examples of biologically active amino compounds include Aceclofenac, Acediasulfone, Alminoprofen, Amisulpride, Amlexanox, Amodiaquine, Amosulalol, Amoxicillin, Amsacrine, Anileridine, Azacyclonol, Baccofen, Balsalazide sodium, Benzocaine, Bromopride, Bumetanide, Carprofen, Carvedilol, Carzenide, Cefprozil, Cinitapride, Clebopride, Clenbuterol, Diclofenac, Ethoxzolamide, Flufenamic acid, Furosemide, lobenzamic acid, locetamic acid, Mefenamic acid, Nadoxolol, D-Norpseudoephedrine and paracetamol.

Examples of biologically active carboxylic acid compounds include Acemetacin, Aceclofenac, Acediasulfone, Adipiodone, Alminoprofen, Amlexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic acid, Mefenamic acid, Naproxen, Nedocromil, Repaglinide, Salazosulfapyridine, Salicylic Acid, Salsalate, Sarpogrelate.

While the above phenolic compounds have various known beneficial uses, they generally are difficult to dissolve in water or the human body or hydrolyze. They are also very difficult to polymerize in the phenolic state. There is also a need to control their rate of action and/or to delay or sustain their efficacy.

SUMMARY OF THE INVENTION

The claimed invention corrects these drawbacks. The present invention provides a method by which biologically active compounds with aromatic hydroxyl, amino or carboxylic acid substituents are functionalized to form hydrolysable, bioabsorbable compounds. This enhances the native value of the biologically active compound by providing the resultant compound or combination of compounds with a specific controlled degradation profile or range enabling controlled release of the compound over an extended, controllable time range. Functionalized compounds derived from polyfunctional aromatic rings containing at least two groups that are the same or different and are independently selected from aromatic hydroxyl, amino or carboxylic acid substituents are readily polymerized to form absorbable or biodegradable polymers. These biodegradable polymers can be prepared with controlled degradation profiles and are suitable for many applications, including biomedical applications, such as stents, stent coatings. This invention greatly extends the usefulness of many biologically active compounds while retaining their inherent biological properties.

The present invention relates to biologically active compounds of the formula:

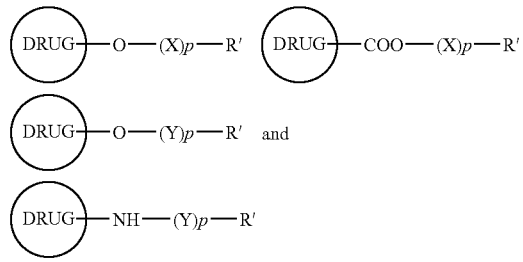

wherein p is between 1 and 4, inclusive, and preferably 1 or 2; R' is a hydrogen, benzyl or alkyl group, the alkyl group being either straight-chained or branched;

represents a moiety comprising 1 to 6 aryl rings that are directly bonded to each other, fused together, or joined through a linking group that when substituted with at least one —OH, —NH$_2$ or —COOH group is a biologically active moiety, examples of which include the residue of phenols, naphthols, flavonoids, isoflavonoids, coumarins, chromones, chalcones, cinnamic acids, simple benzoic acids, indoles, acetophenones, benzophenones, alkaloids, catechins, catechols, hydrocinnamic acids, phenolic acids, resorcinol, hydroquinone, drugs containing phenolic groups, natural products containing phenolic groups, amino acids containing phenolic groups, and drugs containing naphthols;

X represents a member selected from the group consisting of:
 —CH$_2$COO— (glycolic acid moiety)
 —CH(CH$_3$)COO— (lactic acid moiety)
 —CH$_2$CH$_2$OCH$_2$COO— (dioxanone moiety)
 —CH$_2$CH$_2$CH$_2$CH$_2$CH$_2$COO— (caprolactone moiety)
 —(CH$_2$)$_y$COO— where y is one of the numbers 2,3,4 and 6-24 inclusive
 —(CH$_2$CH$_2$O)$_z$CH$_2$COO— where z is an integer between 2 and 24, inclusive;

Y represents a member selected from the group consisting of:
 —COCH$_2$O— (glycolic ester moiety)
 —COCH(CH$_3$)O— (lactic ester moiety)
 —COCH$_2$OCH$_2$CH$_2$O— (dioxanone ester moiety)
 —COCH$_2$CH$_2$CH$_2$CH$_2$CH$_2$O— (caprolactone ester moiety)
 —CO(CH$_2$)$_m$O— where m is one of the numbers 2,3,4 and 6-24 inclusive
 —COCH$_2$O(CH$_2$CH$_2$O)$_n$— where n is an integer between 2 and 24, inclusive;
and
R' is a hydrogen, benzyl or alkyl group, the alkyl group being either straight-chained or branched. The inventive compounds are defined as being functionalized with the defined X, Y and R' substituents, which alter the native value or efficacy of the pre-functionalized compound by modifying the onset or length of action thereof.

Another aspect of the invention provides a method by which biologically active drug moieties that are substituted with at least one —OH, —NH$_2$ or —COOH group may be functionalized with a moiety selected from glycolic acid, lactic acid, p-dioxanone, ε-caprolactone, —(CH$_2$)$_y$COO—, where y is one of the integers 2,3,4 and between 6 and 24 inclusive, and —(CH$_2$CH$_2$O)$_z$CH$_2$COO—, wherein z is an integer between 2 and 24 inclusive, to form a new chemical entity. The resultant functionalized compound is more hydrolysable and biodegradable than the pre-functionalized compound, providing controlled release of the active component over a time period from several weeks to four years, depending on the functionalized moiety or combination of moieties selected for the reaction.

A preferred biologically active hydroxy compound that can be used to prepare a functionalized drug of the invention is acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, bupheniode, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochloride, ketobemidone, khellin, labetalol, lactylphenetidin, levodopa. levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, α-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

Preferred biologically active amine compounds that can be used to prepare a functionalized drug of the invention include Aceclofenac, Acediasulfone, Alminoprofen, Amisulpride, Amlexanox, Amodiaquine, Amosulalol, Amoxicillin, Amsacrine, Anileridine, Azacyclonol, Baccofen, Balsalazide sodium, Benzocaine, Bromopride, Bumetanide, Carprofen, Carvedilol, Carzenide, Cefprozil, Cinitapride, Clebopride, Clenbuterol, Diclofenac, Ethoxzolamide, Flufenamic acid, Furosemide, Iobenzamic acid, Iocetamic acid, Mefenamic acid, Nadoxolol, D-Norpseudoephedrine and paracetamol.

A preferred biologically active carboxylic acid compound that can be used to prepare a polymer of the invention is Acemetacin, Aceclofenac, Acediasulfone, Adipiodone, Alminoprofen, Amlexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic cid, Mefenamic acid, Naproxen, Nedocromil, Repaglinide, Salazosulfapyridine, Salicylic Acid, Salsalate, Sarpogrelate.

In a further aspect of the invention one can blend compounds comprising one or more of the functionalized biologically active compounds of the present invention with one or more other functionalized biologically active compounds of the present invention or pre-functionalized biologically active compounds.

The present invention also combines two monofunctional drugs to form a dimer of two drug molecules, which may be the same or different. One or both drug molecules may be functionalized prior to formation of the dimer. Dimer drugs according to the present invention have the following structure:

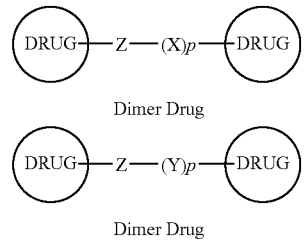

Dimer Drug

Dimer Drug wherein each

is the same or different and is the same as described above, X is selected from.

—CH$_2$COO— (glycolic acid moiety),
—CH(CH$_3$)COO— (lactic acid moiety),
—CH$_2$CH$_2$OCH$_2$COO— (dioxanone moiety),
—CH$_2$CH$_2$CH$_2$CH$_2$CH$_2$COO— (caprolactone moiety),
—(CH$_2$)$_y$COO— where y is one of the numbers 2,3,4 or 6-24 inclusive, and
—(CH$_2$CH$_2$O)$_z$CH$_2$COO— where z is an integer between 2 and 24, inclusive;

Y is selected from:
—COCH$_2$— (glycolic acid moiety);
—COCH(CH$_3$)O— (lactic acid moiety);
—COCH$_2$CH$_2$OCH$_2$O— (dioxanone moiety);
—COCH$_2$CH$_2$CH$_2$CH$_2$CH$_2$O— (caprolactone moiety);
—CO(CH$_2$)$_y$O— where y is one of the numbers 2,3,4 and 6-24 inclusive; and
—CO(CH$_2$CH$_2$O)$_z$CH$_2$O— where z is an integer between 2 and 24, inclusive;

Z is O, COO or NH; and p is 1-4.

The present invention also provides biologically active polyfunctionalized compounds prepared from biologically active compounds with two or more of the same or different aromatic —OH, NH$_2$ or COOH groups. The polyfunctionalized compounds are oligomers and polymers having the formula:

R'—W—[-DRUG-W—]$_a$—R' wherein "a" is an integer between 2 and 2000, inclusive, W is selected from —O—(X)$_p$—, —COO—(X)$_p$—, —O—(Y)$_p$— and —NH—(Y)$_p$—, each -DRUG-W— unit may be the same or different, and DRUG, R', X, Y, and p are the same as described above.

Another aspect of the invention is to create polymers from the functionalized biologically active compounds of this invention that are polyfunctional, that is those species having more than one group selected from —OH, —NH$_2$ and —COOH groups. Polymers of the functionalized biologically active compounds have specific ranges over which they release the biologically active moiety. One can blend polymers made from functionalized biologically active compounds according to the present invention with one or more other polymerized or non-polymerized functionalized biologically active compounds according to the present invention, or non-functionalized compounds, to obtain the release range desired for the specific application into the body of a mammalian, including a human, or the environment. This release range varies with the species used for functionalization. The combinations or blends of these entities may comprise an amount of from 0.5% to 99.5% of each species.

The functionalized biologically active compounds have potential application in the same or similar areas as the non-functionalized biologically active compounds, since the compounds retain the innate properties of the active compound, for example, as enhanced drugs, cancer preventing agents, nutrition supplements, nutriceuticals, antioxidants, controlled release preparations, cosmetic applications, food stuffs, flavors, coatings, drug intermediates, solvents for drugs, new monomers for polymerization, and when polymerized, as polymers for biomedical applications, drugs, nutrition supplements, nutriceuticals, drug delivery, cosmetic applications, flavors, and coatings. This list of uses is provided as examples and is not meant to be all-inclusive. In addition, the active portion of the functionalized compound has improved bioavailability, increased solubility, and can be further reacted or sometimes polymerized, thus increasing their usefulness.

DETAILED DESCRIPTION OF THE PREFERRED EMBODIMENT

Biologically active compounds with —COOH groups can be functionalized with glycolic acid moieties according to the following process:

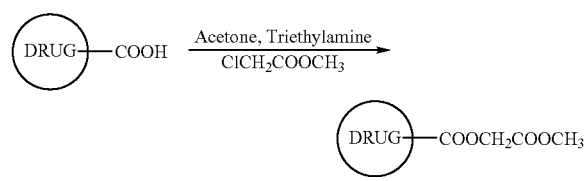

This process can be repeated to increase the degree of glycolic acid functionalization. Similar processes can be employed to functionalize such compounds with a moiety selected from lactic acid, p-dioxanone, ε-caprolactone, —(CH$_2$)$_y$COO—, where y is one of the integers 2,3,4 and between 6 and 24 inclusive, and —(CH$_2$CH$_2$O)$_z$CH$_2$COO—, wherein z is an integer between 2 and 24 inclusive.

Biologically active compounds with —OH groups can be functionalized with glycolic acid moieties according to the following processes.

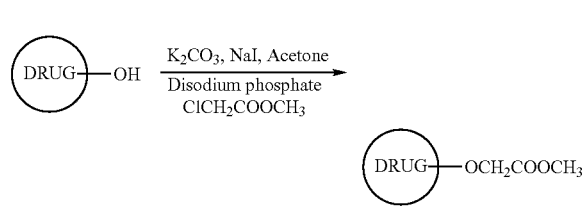

This process can also be repeated to increase the degree of glycolic acid functionaliztion. Again, similar processes can be employed to functionalize such compounds with a moiety selected from lactic acid, p-dioxanone, ε-caprolactone, —(CH$_2$)$_y$COO—, wherein y is an integer selected from 2, 3 or 4 or between 6 and 24 inclusive, and —(CH$_2$CH$_2$O)$_z$CH$_2$COO—, wherein z is an integer between 2 and 24 inclusive.

Biologically active compounds with —OH groups can also be functionalized with glycolic acid moieties according to the following process:

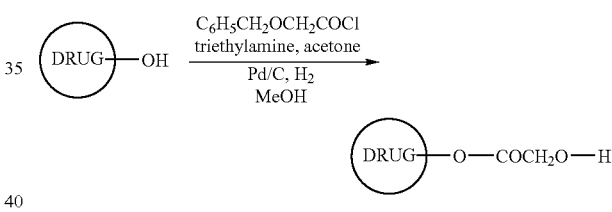

This process can also be repeated to increase the degree of glycolic acid functionaliztion. Again, similar processes can be employed to functionalize such compounds with a moiety selected from lactic acid, p-dioxanone, ε-caprolactone, —CO(CH$_2$)$_y$OH, wherein y is an integer selected from 2, 3 or 4 or between 6 and 24 inclusive, and —CO(CH$_2$CH$_2$O)$_z$CH$_2$OH, wherein z is an integer between 2 and 24 inclusive.

Biologically active compounds with —NH$_2$ groups can also be functionalized with glycolic acid moieties according to the following process:

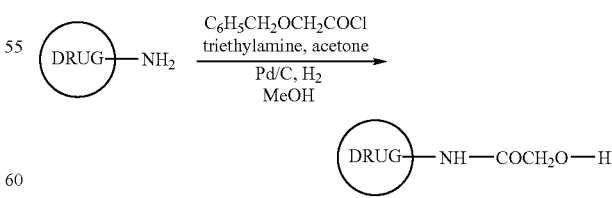

This process can also be repeated to increase the degree of glycolic acid functionalization. Again, similar processes can be employed to functionalize such compounds with a moiety selected from lactic acid, p-dioxanone, ε-caprolactone, —CO(CH$_2$)$_y$OH, wherein y is an integer selected from 2, 3 or 4 or between 6 and 24 inclusive, and —CO(CH$_2$CH$_2$O)$_z$CH$_2$OH, wherein z is an integer between 2 and 24 inclusive.

Dimers can be formed between the same or different functionalized biologically active compounds. Dimers according to the present invention have the following structure:

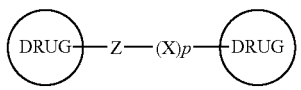

Dimer Drug

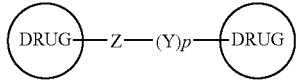

Dimer Drug wherein each

is the same or different and is the same as described above,
—X is selected from.
—CH$_2$COO— (glycolic acid moiety),
—CH(CH$_3$)COO— (lactic acid moiety),
—CH$_2$CH$_2$OCH$_2$COO— (dioxanone moiety),
—CH$_2$CH$_2$CH$_2$CH$_2$CH$_2$COO— (caprolactone moiety),
—(CH$_2$)$_y$COO— where y is one of the numbers 2,3,4 or 6-24 inclusive, and
—(CH$_2$CH$_2$O)$_z$CH$_2$COO— where z is an integer between 2 and 24, inclusive;

Y is selected from:
  —COCH$_2$O— (glycolic acid moiety);
  —COCH(CH$_3$)O— (lactic acid moiety);
  —COCH$_2$CH$_2$OCH$_2$O— (dioxanone moiety);
  —COCH$_2$CH$_2$CH$_2$CH$_2$O— (caprolactone moiety);
  —CO(CH$_2$)$_y$O— where y is one of the numbers 2,3,4 and 6-24 inclusive; and
  —CO(CH$_2$CH$_2$O)$_z$CH$_2$O— where z is an integer between 2 and 24, inclusive;

Z is O, COO or NH; and p is 1-4.

One example of a method by which dimers of different biologically active compounds may also be formed in which one Z is O and the other is NH is depicted below:

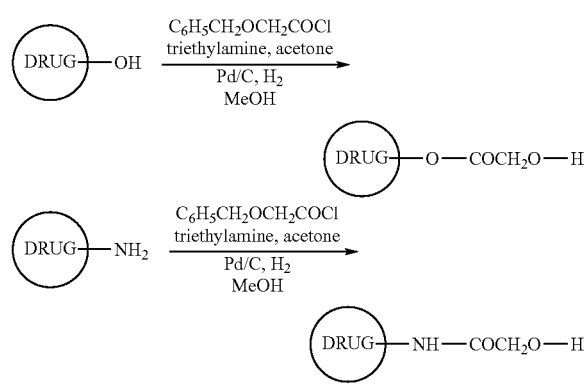

A method in which a compound can be prepared in which n is two is depicted below. The first step in which a biologically active compound with a hydroxyl group is functionalized with benzyl glycolic acid chloride is repeated a second time

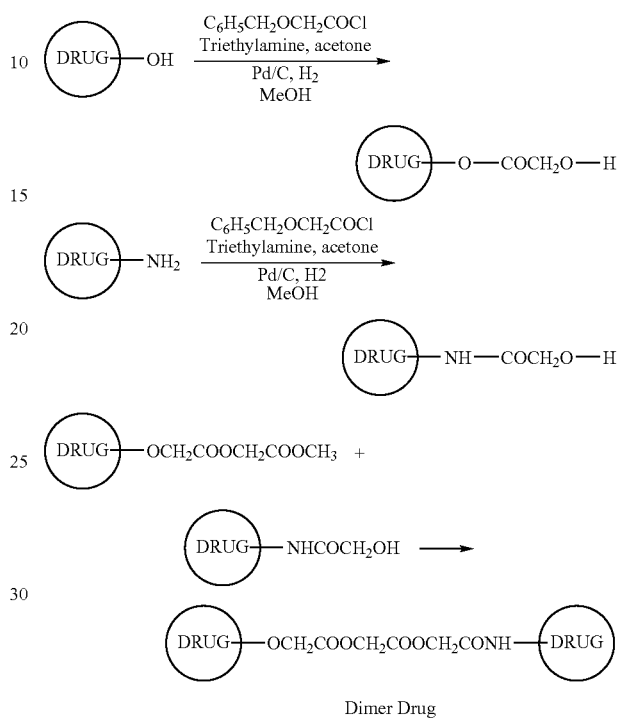

Other examples for the preparation of dimer drugs are illustrated below:

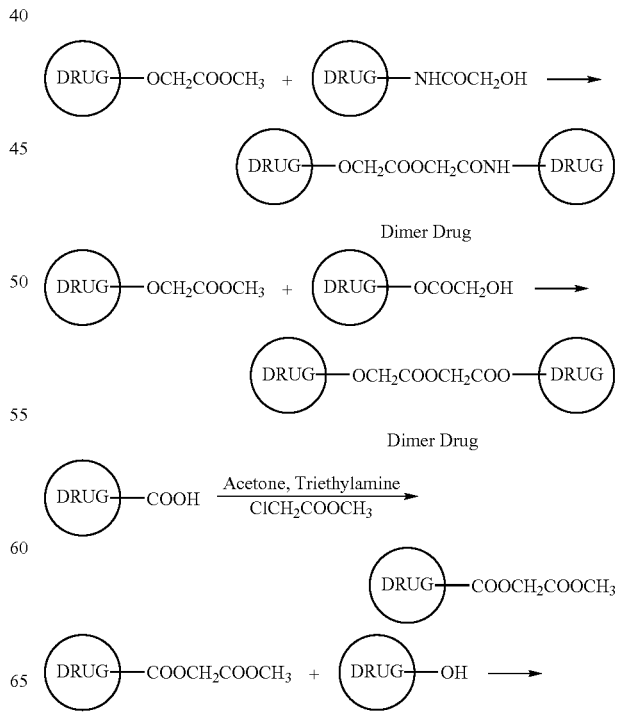

-continued

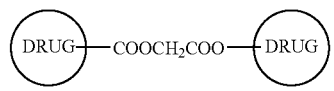

Dimer Drug

Other dimers that may be formed from the functionalized compounds of the present invention will be readily apparent to the skilled artisan.

Biologically active compounds containing a plurality of groups independently selected from OH, NH$_2$ and COOH can also be polyfunctionalized. Methods by which compounds with two hydroxyl groups and with a hydroxyl group and an amino group are difunctionalized are depicted below:

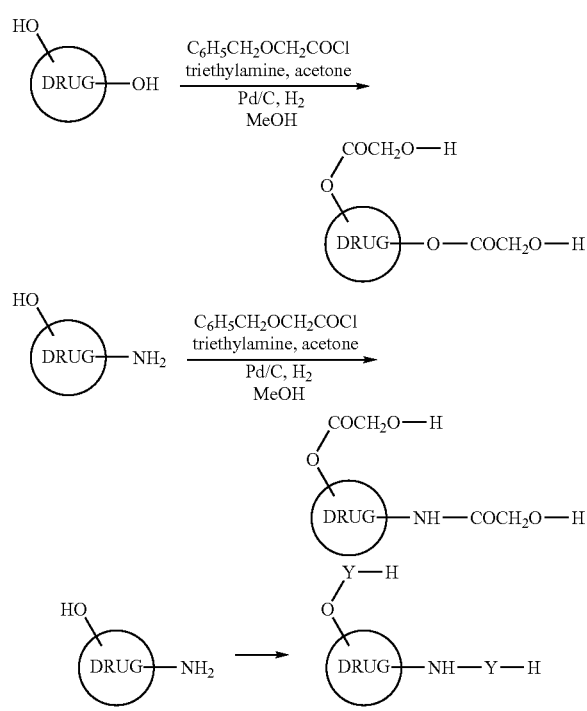

The functionalization steps can be repeated to increase the degree of difunctioalization. Difunctionalized compounds are thus prepared having the formula:

wherein R', W and DRUG are the same as described above, and each R' and W may be the same or different. Other examples of ways by which difunctionalized compounds may be prepared are depicted below:

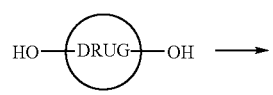

-continued

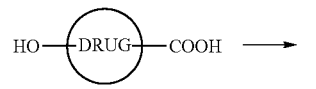 ⟶

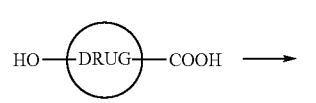 ⟶

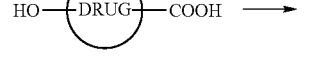 ⟶

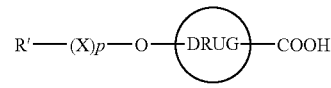

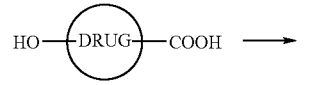 ⟶

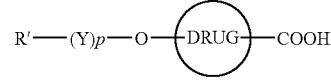

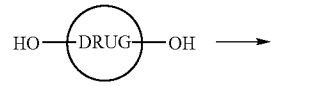 ⟶

 ⟶

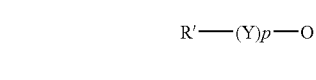 ⟶

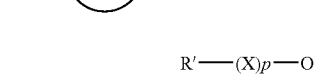 ⟶

 ⟶

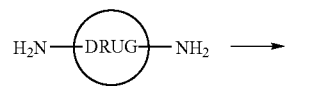 ⟶

 ⟶

Where p=1-4, more preferably 1-2

A preferred biologically active dihydroxy compound that can be used to prepare a polymer of the invention is: Adrenalone, Alfuzosin, Alibendol, Amrubicin, Apomorphine, Bamethan, Benzquinamide, Bevantolol, Bifluranol, Bisacodyl, Brodimoprim, Bunazosin, Bupheniode, Carbidopa, Carbuterol, Cyclofenil, Cyclovalone, Daunorubicin, Dichlorophen, Dienestrol, Diethylstilbestrol, Dimestrol, Dithranol, Donepezil, Doxefazepam, Doxorubicin, Entacapone, Epinepheine, Epirubicin, Esomeprazole, Etamivan, Etamsylate, Etilefrine, Ezetimibe, Fenticlor, Fluorescein, Folescutol, Formoterol, Gefitinib, Hexestrol, Hexylresorcinol, Hydroxyethyl salicylate, Ifenprodil, Isoetarine, Isoxsuprine, Itopride. HCl, Khellin, Labetalol, Mitoxantrone, Morclofone, Moxaverine, Normolaxol, Omeprazole, Oxilofrine, Oxepertine, Phenacaine, Phenolphthalein, Prazosin, Tolcapone, Vesnarinone, Vetradutine A preferred biologically active diamino compound that can be used to prepare a polymer of the invention is: Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine A preferred biologically active hydroxy/amino compound that can be used to prepare a polymer of the invention is: Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, paracetamol A preferred biologically active dicarboxylic acid compound that can be used to prepare a polymer of the invention is: Adipiodone, Cromoglicic acid, Eprosartan, Iocarmic acid, Iodoxamic acid, Ioglycamic acid, Iotroxic cid, Nedocromil A preferred biologically active hydroxy/carboxylic acid compound that can be used to prepare a polymer of the invention is: Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, Sarpogrelate.

A preferred biologically active amino/carboxylic acid compound that can be used to prepare a polymer of the invention is: Aceclofenac, Acediasulfone, Alminoprofen, Amlexanox, Anileridine, Baccofen, Balsalazide sodium, Benzocaine, Bumetanide, Carprofen, Carzenide, Diclofenac, Flufenamic acid, Furosemide, Iobenzamic acid, Iocetamic acid, Mefenamic acid.

The difunctionalized compounds can then be linked together by conventional means readily apparent to those of ordinary skill to form oligomers and polymers having the formula:

wherein "a," R', W and DRUG are the same as described above, and each R', W and DRUG may be the same or different.

Trifunctionalization is accomplished by the same techniques employed for producing monofunctionalized and difunctionalized compounds. The following schemes illustrate how biologically active compounds with three substituents independently selected from aromatic —OH, —NH₂ and —COOH may be trifunctionalized:

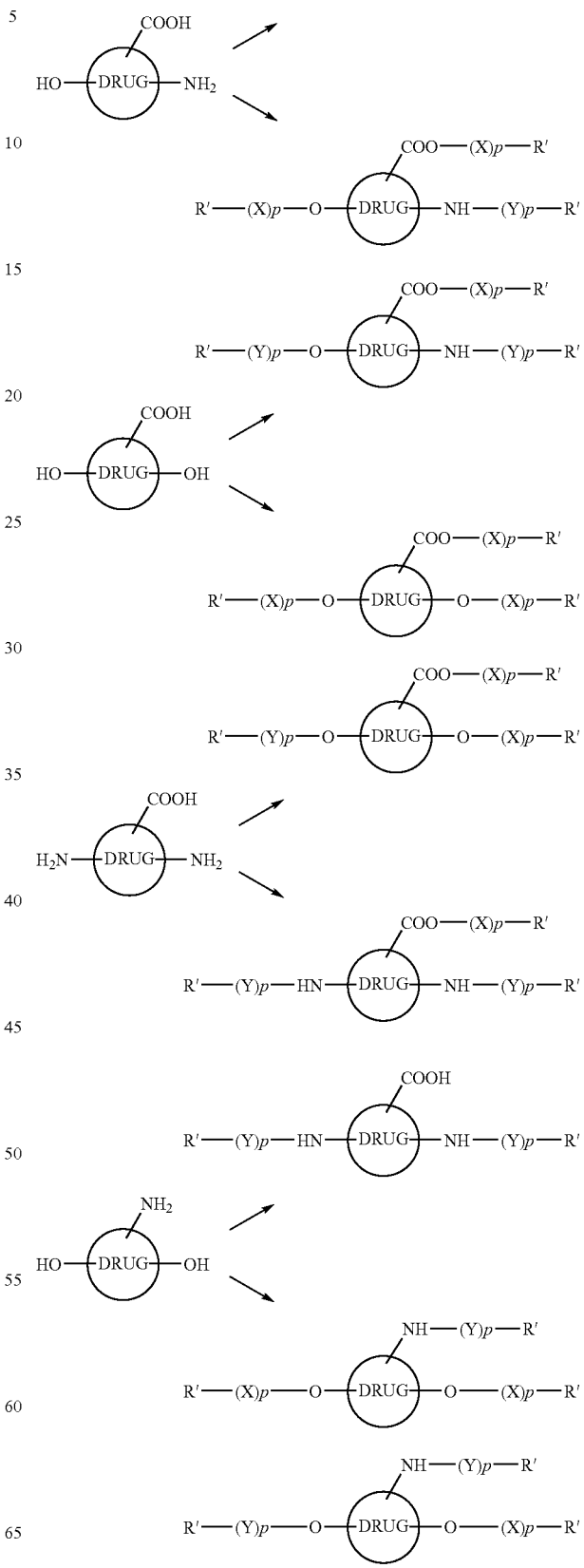

-continued

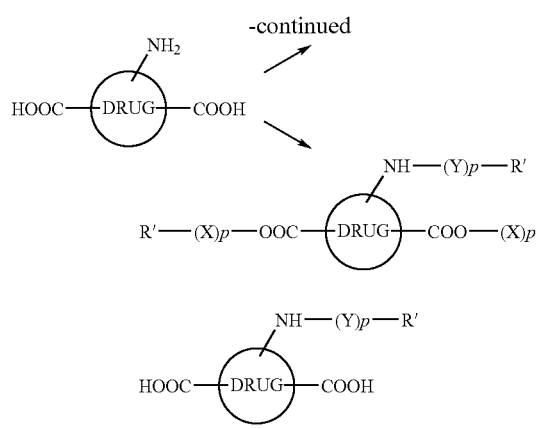

Where p is 1-4, more preferably 1-2.

Crosslinked polymers with biological properties can be prepared from the trifunctionalized biologically active compounds of the present invention by conventional means. From the preparation of difunctionalized and trifunctionalized compounds according to the present invention, the preparation higher polyfunctionalized compounds and polymers thereof will be readily apparent to one of ordinary skill in the art.

A preferred biologically active multifunctional (hydroxyl, amino, and/or carboxylic acid) compound that can be used to prepare a polymer of the invention is p-Aminosalicylic acid, Benserazide, Buflomedil, Chlorotrianisene, Cianidanol, Cinepazet, Cinepazide, Cynarine, Denopamine, Deserpidine, Dextrothyroxine, Diacerein, Dilazep, Dimoxyline, Dibutamin, Dopamine, Dopexamine, Doxazosin, Epanolol, Ethaverine, Exifone, Fenoldopam mesilate, Fenoterol, Fenoxedil, Flopropione, Gallopamil, Gatifloxacin, Gentisic acid, Hexobendine, Hexoprenaline, Isoprenaline, Levodopa, Levothyroxine, Lobenzarit, Mebeverine, Mesalazine, Methoxamine, Methyldopa, Metirosine, Midodrine, Mofezolac, Nadolol, Norfenefrine, Octopamine, Olsalazine sodium, Orciprenaline, Oxitriptan, Papaverine, Protokylol, Pyritinol, Reproterol, Rescimetol, Rescinnamine, Reserpine, Rimiterol, Ritodrine, Salbutamol, Salmeterol, Silibinin, Sulmetozin, Temoporfin, Terazosin, Terbutaline, Tetroxoprim, Theodrenaline, Tofisopam, Tranilast, Tretoquinol, Trimetazidine, Trimethobenzamide, Trimethoprim, Trimetozine, Trimetrexate glucuronate, Tritoqualine, Trixipide, Valrubicin, Verapamil The functionalized biologically active compounds of the invention, and the oligomers and polymers thereof, are further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound being used. The formulations of a pharmaceutical composition are typically admixed with one or more pharmaceutically or veterinarially acceptable carriers and/or excipients as are well known in the art. Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Compositions of the present invention suitable for parenteral administration conveniently comprise sterile aqueous preparations of the active compounds, which preparations are preferably isotonic with the blood of the intended recipient.

Formulations suitable for rectal administration are preferably presented as unit dose suppositories. Formulations suitable for vitreal administration may be presented as bioabsorbable coatings for implantable medical devices, injectables, liquids, gels or suspensions.

Formulations or compositions suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations suitable for transdermal administration may be presented as discrete patches adapted to remain in intimate contact with the epidermis of the recipient for a prolonged period of time.

The active compounds may be provided in the form of foodstuffs, such as being added to, admixed into, coated, combined or otherwise added to a foodstuff. The term foodstuff is used in its widest possible sense and includes liquid formulations such as drinks including dairy products, bioabsorbable chewing gums, and other foods, such as health bars, desserts, etc. Food formulations containing compounds of the invention can be readily prepared according to standard practices.

Compounds of the formula used as medicaments are typically administered in a manner and amount as is conventionally practiced. See, for example, Goodman and Gilman, *The Pharmaceutical Basis of Therapeutics*, current edition. Compounds of the present invention have potent antioxidant activity and increased acidity of their phenolic component as well as the improved biodegradation provided by the functionalization and thus find wide application in pharmaceutical and veterinary uses, in cosmetics such as more effective skin creams to prevent skin ageing, in sun screens, in foods, health drinks, nutritional supplements, shampoos, and the like.

POLYMERS OF THE INVENTION

The biocompatible, biodegradable polyesters, polyesteramides, polyamides, and polyurethanes of the invention are useful in a variety of applications where delivery of a biologically active compound is desired. Examples of such applications include, but are not limited to, medical, dental and cosmetic uses.

The polymers of the invention may be prepared in accordance with methods commonly employed in the field of synthetic polymers to produce a variety of useful products with valuable physical and chemical properties. The polymers can be readily processed into pastes or solvent cast to yield films, coatings, microspheres and fibers with different geometric shapes for design of various medical implants, and may also be processed by compression molding and extrusion.

Polyesters, polyesteramides and polyamides prepared in accordance with the present invention have average molecular weights of about 1500 to about 100,000 Daltons, calculated by Gel Permeation Chromatography (GPC) relative to narrow molecular weight polystyrene standards. Preferred polyesters and polyamides have average molecular weights of about 1500 to about 100,000 calculated by Gel Permeation Chromatography (GPC) relative to narrow molecular weight polystyrene standards. Preferred polyesters, polyesteramides, polyurethanes and polyamides have average molecular weights of about 2000 up to about 40,000.

Medical implant applications include the use of polyesters, polyesteramides, polyurethanes or polyamides to form shaped articles such as vascular grafts and stents, bone plates, sutures, implantable sensors, implantable drug delivery devices, stents for tissue regeneration, and other articles that decompose into non-toxic components within a known time period.

Polymers of the present invention can also be incorporated into oral formulations and into products such as skin moisturizers, cleansers, pads, plasters, lotions, creams, gels, ointments, solutions, shampoos, tanning products and lipsticks for topical application.

Although the invention provides homopolymers that are prepared from suitably functionalized biologically active compounds, these polymers can be further polymerized with lactone monomers, such as glycolide, lactide, caprolactone, trimethylene carbonate and/or p-dioxanone, and the resulting absorbable polymers have potential applications, including biomedical applications, such as medical devices, including implantable devices, and drug delivery.

Functionalized phenolics with at least two reactive sites are polymerized with the functionalization molecules to form absorbable polymers, including but not limited to polyesters, polyester amides, and polyurethanes by simple polycondensation reactions. The absorption profile will depend upon the functionalization species used. Glycolic acid based polymers hydrolyze faster than p-dioxanone based, where as lactic acid and caprolactone based polymers take much longer to hydrolyze than glycolic acid and p-dioxanone based polymers. The desired time range may be obtained by using a combination of functionalized phenolic compounds, that is, a blend of two or more functionalized compounds made from any two or more of the species glycolide, lactide, dioxanone and polydioxanone combined with one phenolic compound. These polymers can be used in various compositions or can be further polymerized with lactone monomers, such as glycolide, lactide, caprolactone, trimethylene carbonate and p-dioxanone, and the resulting absorbable polymers have potential applications, including biomedical applications such as medical devices, including implantable devices, and drug delivery systems.

Biologically Active Compounds

The term "biologically active compound" includes therapeutic agents that provide a therapeutically desirable effect when administered to an animal (e.g. a mammal, such as a human). Biologically active compounds that can be incorporated into the polymers of the invention possess at least two functional groups that can each be incorporated into an ester, or amide linkage of a polymer (as discussed in detail below), such that, upon hydrolysis of the polymer, the therapeutic agent is obtained. These groups can independently be a hydroxy group (—OH), an amine group (—NHR), or a carboxylic acid (—COOH).

The biologically active compounds can also comprise other functional groups (including hydroxy groups, amine groups, and carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

Incorporated as phenolics forming the embodiments of this invention are all biologically active phenolic compounds mentioned in this document, especially those containing amine groups, carboxylic acid groups and amino acid moieties and all phenolic compounds contained in the following texts:

1. Shahidi, Ferriodoon and Marian Naczk, *Phenolics in Food and Nutriceuticals*, Boca Raton, Fla.: CRC Press, 2003.
2. Kleemann, A. et al, *Pharmaceutical Substances*, 4th Edition, New York: Thieme (2000).
3. *Phenolic Compounds in Food and Their Effects on Health II; Antioxidants and Cancer Prevention*, ACS Symposium Series No. 507, Washington, D.C.: ACS, 1992.
4. *Food Phytochemicals for Cancer Prevention I*, ACS Symposium Series N. 546, Washington, D.C.: ACS, 1994.
5. *ROMPP Encyclopedia Natural Products*, New York: Thieme, 2000.
6. *The Merck Index*, $12^{th}$ edition, Rahway, N.J.: Merck and Company, 1996.
7. *A Single Source for Flavonoids and Coumarins* (2005-2006), INDOFINE Chemical Company, Inc.

All information regarding biologically active phenolics contained in these books is incorporated into this patent by reference. One skilled in the art can readily select therapeutic agents that possess the necessary functional groups for incorporation into the polymers of the invention from these lists.

Therapeutic agents that can be incorporated into the polymers of the invention include suitably functionalized analgesics or general or local anesthetics, anti-convulsants, anti-diabetic agents, anti-fibrotic agents, anti-infectives, anti-bacterials, anti-fungals, anti-neoplastics, cardioprotective agents, cardiovascular agents, anti-thrombotics, central nervous system stimulants, cholinesterase inhibitors, contraceptives, deodorants, dopamine receptor agonists, erectile dysfunction agents, fertility agents, gastrointestinal agents, gout agents, hormones, immunomodulators, immunosuppressives, migraine agents, non-steriodal anti-inflammatory drugs (NSAIDs), motion sickness agents, muscle relaxants, nucleoside analogs, neurodegenerative agents (e.g, Parkinson's disease), obesity agents, ophthalmic agents, osteoporosis agents, parasympatholytics, parasympathommetics, anti-anesthetics, prostaglandins, psychotherapeutic agents, respiratory agents, sedatives, hypnotics, skin and mucous membrane agents, smoking cessation agents, sympatholytics, urinary tract agents, vaginal agents, and vasodilators (see Physicians' Desk Reference, 55 ed., 2001, Medical Economics Company, Inc., Montvale, N.J., pages 201-202)

Formulations

The polymers of the invention can be formulated as pharmaceutical compositions and administered to a mammalian host, such as a human patient in a variety of forms adapted to the chosen route of administration, i.e., orally rectally, or parenterally, by intravenous, intramuscular, intraperitoneal, intraspinal, intracranial, topical or subcutaneous routes. For some routes of administration, the polymer can conveniently be formulated as micronized particles.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of the compositions and preparations may, of course, be varied and may conveniently be between about 2 to about 80% of the weight and preferably 2 to about 60% of a given unit dosage form. The amount of polymer in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The polymer may also be administered intravenously, intraspinally, intracranially, or intraperitoneally by infusion or injection. Solutions of the polymer can be prepared a suitable solvent such as an alcohol, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile solutions or dispersions or sterile powders comprising the polymer containing the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polymer in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present polymers can be applied in pure form. However, it will generally be desirable to administer them as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the polymers can be determined by comparing their in vitro activity, and in vivo activity of the therapeutic agent in animal models. Methods for the extrapolation of effective dosages in mice, and other animals, to humans are known to the art; for example, see U.S. Pat. No. 4,938,949. Additionally, useful dosages can be determined by measuring the rate of hydrolysis for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Combination Therapies

The polymers of the invention are also useful for administering a combination of therapeutic agents to an animal. Such a combination therapy can be carried out in the following ways: 1) a second therapeutic agent can be dispersed within the polymer matrix of a polymer of the invention, and can be released upon degradation of the polymer; 2) a second therapeutic agent can be appended to a polymer of the invention (i.e. not in the backbone of the polymer) with bonds that hydrolyze to release the second therapeutic agent under physiological conditions; 3) the polymer of the invention can incorporate two therapeutic agents into the polymer backbone or 4) two polymers of the invention, each with a different therapeutic agent can be administered together (or within a short period of time).

Thus, the invention also provides a pharmaceutical composition comprising a polymer of the invention and a second therapeutic agent that is dispersed within the polymer matrix of a polymer of the invention. The invention also provides a pharmaceutical composition comprising a polymer of the invention having a second therapeutic agent appended to the polymer (e.g. with bonds that will hydrolyze to release the second therapeutic agent under physiological conditions).

The polymers of the invention can also be administered in combination with other therapeutic agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier.

The following non-limiting examples set forth herein below illustrate certain aspects of the invention. All parts and percentages are by weight unless otherwise noted.

EXAMPLES

Example 1

2-Methoxycarbonylmethoxy-benzoic acid methyl ester (1)

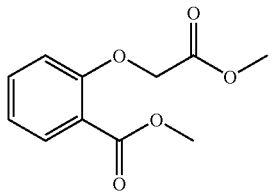

To a mixture of methyl salicylate (100 g, 657 mmol) and anhydrous $K_2CO_3$ (360 g, 2.605 mol) in anhydrous acetone (1000 ml) was added methyl chloroacetate (94 g, 866 mmol) and refluxed for 36 hours. The acetone was distilled off and water (1200 ml) was added. Crude 1 was extracted into chloroform, dried over $Na_2SO_4$ distilled and purified by column chromatography on silica gel using hexane as eluant to give pure 1 (25 grams, 17%) as a light yellow syrup.

The structure was confirmed by NMR. $^1$HNMR (CDCl$_3$) 3.79(s, 3H,ester), 3.88 (s,3H,ester), 4.70(s,2H,OC$\underline{H}_2$), 6.88 (dd,1H,Ar), 7.03 (m,1H,Ar), 7.42(m,1H,Ar), 7.81(dd,1H,Ar)

Example 2

2-(1-Methoxycarbonylethoxy)benzoic acid methyl ester (2)

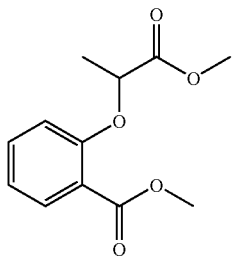

To a mixture of methyl salicylate (100 g, 657 mmol), anhydrous $K_2CO_3$ (360 gr, 2.605 mol) and sodium iodide (5 g, 33.3 mmol) in anhydrous acetone (1000 ml) was added methyl 2-chloro propionate (104 g, 849 mmol) and refluxed for 48 hours. Acetone was distilled off and water (1200 ml) was added. Crude 2 was extracted into ethyl acetate, dried over $Na_2SO_4$, distilled and purified by column chromatography on silica gel using hexane as eluant to give pure 2 (35 grams, 22.4%) as a light yellow syrup. The melting point was measured for the products by using Polmon (MP 96) melting point apparatus, and IR was run using Perkin Elmer FTIR Spectrophotometer, Model: Spectrum RXI FTIR. For all compounds, NMR was run using Varian 200 MHz and tetramethyl-silane as the internal standard. The structure for this was confirmed by NMR.

HNMR (CDCl$_3$) 1.58(d, 3H,CH$_3$), 3.65(s,3H,ester), 3.82 (s,3H,ester), 4.72(q,1H,CH), 6.78 (d,1H,Ar), 6.85(m,1H,Ar), 7.32(m,1H,Ar), 7.74(d,1H,Ar)

Example 3

2-(5-Methoxycarbonylpentyloxy)benzoic acid methyl ester (3)

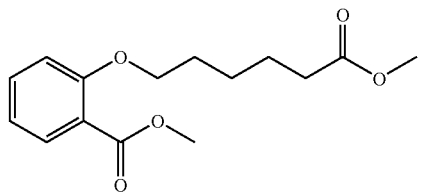

To a mixture of methyl salicylate (50 g, 329 mmol), anhydrous $K_2CO_3$ (180 grams, 1.30 mol) and sodium iodide (5 grams, 33.3 mmol) in anhydrous acetone (600 ml) was added methyl 6-bromo hexanoate (76 g, 364 mmol) and refluxed for 40 hours. Acetone was distilled off and water (750 ml) was added. Crude 3 was extracted into ethyl acetate, dried over $Na_2SO_4$, distilled and purified by column chromatography on silica gel using hexane as eluant to give pure 3 (55 grams, 60%) as a light yellow syrup. The structure was confirmed by NMR.

$^1$HNMR (CDCl$_3$) 1.60 (m, 2H,CH$_2$), 1.72 (m, 2H,CH$_2$), 1.77 (m, 2H,CH$_2$), 2.35 (t, 2H,CH$_2$), 3.66 (s,3H,ester), 3.88 (s,3H,ester), 4.02(t,2H,OCH$_2$), 6.90(m,2H,Ar), 7.38(m,1H, Ar), 7.74(d,1H,Ar)

Example 4

2,5-Bismethoxycarbonylmethoxybenzoic acid methyl ester (4)

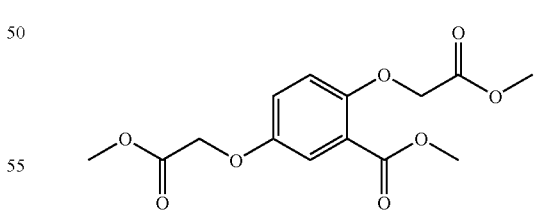

To a mixture of methyl 2,5-dihydroxybenzoate (34 g, 202 mmol), anhydrous $K_2CO_3$ (204 g, 1.476 mol) and sodium iodide (5 grams, 33.3 mmol) in anhydrous acetone (1000 ml) was added methyl chloroacetate (60.7 grams, 559 mmol) and refluxed for 20 hours. Acetone was distilled off and water (1500 ml) was added. Crude 4 was filtered, dried and recrystallised from toluene to give pure 4 (50.5 g, 80%) as a cream colored powder. The melting point was found to be 90-94° C. The structure was confirmed by NMR.

¹HNMR (CDCl₃) 3.78 (s, 3H, ester), 3.80 (s, 3H, ester), 3.89 (s, 3H, ester), 4.59 (s, 2H, OC$\underline{H_2}$), 4.63(s, 2H, OC$\underline{H_2}$), 6.88 (d, 1H, Ar), 7.02 (dd, 1H, Ar), 7.32 (d, 1H, Ar)

Example 5

2-(6-Hydroxynaphthalen-2-yl)propionic acid (5)

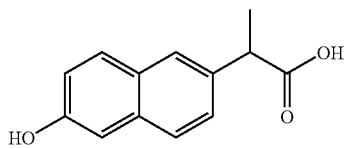

A mixture of Naproxen (500 g, 2.774 mmol) and 48% HBr (1500 ml) was refluxed for 10 hours, poured onto ice water (3000 ml) and stirred for 30 minutes. Crude 5 was filtered, dried (380 grams, 81%) and used as such for next stage.

Example 6

2-(6-Hydroxynaphthalen-2-yl)-propionic acid methyl ester (6)

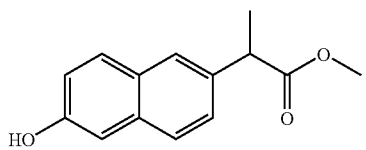

To a solution of methanol (2100 ml) and sulphuric acid (84 ml) was added 2-(6-Hydroxynaphthalen-2-yl)-propionic acid 5 (420 g, 1.944 mmol), and refluxed for 6 hours. Methanol (1000 ml) was distilled off and the cooled reaction mass was poured onto ice water (3000 ml). Crude 6 was filtered, dried and recrystallised from a mixture of ethyl acetate:hexane (1:5) to give pure 6 (400 g, 89.5%) as a white fluffy powder. The melting point found to be 89.5-92° C. The structure was confirmed with IR and NMR.

¹HNMR (CDCl₃) 1.60 (d, 3H, CH₃), 3.70 (s, 3H, ester), 3.88 (q, 1H, CH), 5.36 (bs, 1H, OH), 7.08 (m, 2H, Ar), 7.48 (m, 1H, Ar), 7.65 (m, 3H, Ar)

Example 7

2-(6-Methoxycarbonylmethoxy-naphthalen-2-yl)-propionic acid methyl ester (7)

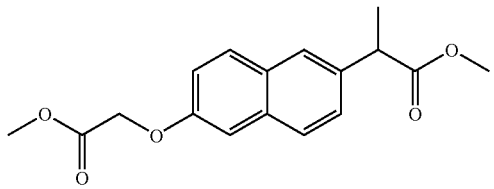

To a mixture of 2-(6-Hydroxy-naphthalen-2-yl)-propionic acid methyl ester 6 (175 g, 761 mmol), anhydrous K₂CO₃ (315 gr, 2.279 mmol) and sodium iodide (21 grams, 140 mmol) in anhydrous acetone (2000 ml) was added methyl chloroacetate (104 g, 958 mmol) and refluxed for 6 hours. Acetone was distilled off and water (1500 ml) was added. Crude 7 was extracted into ethyl acetate, dried over Na₂SO₄, distilled and purified by column chromatography on silica gel using benzene as eluant to give pure 10 (125 g, 54.3%) as a pale yellow syrup. The structure was confirmed with NMR.

¹HNMR (CDCl₃) 1.57 (d, 3H, CH₃), 3.64 (s, 3H, ester), 3.78 (s, 3H, ester), 3.80 (q, 1H, CH), 4.70 (s, 1H, Ar), 7.22 (d, 1H, Ar), 7.36 (m, 2H, Ar), 7.68 (m, 3H, Ar)

Example 8

2-[6-(1-Methoxycarbonyl-ethoxy)-naphthalen-2-yl]-propionic acid methyl ester (8)

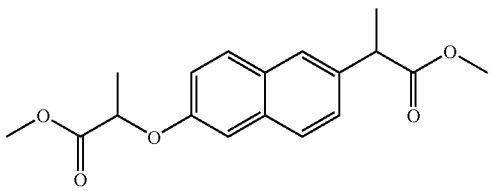

To a mixture of 2-(6-Hydroxy-naphthalen-2-yl)-propionic acid methyl ester 7 (150 g, 652 mmol), anhydrous K₂CO₃ (455 gr, 3.292 mol) and sodium iodide (22.5 grams, 150 mmol) in anhydrous acetone (2000 ml) was added methyl 2-chloropropionate (107.5 g, 877 mmol) and refluxed for 50 hours. Acetone was distilled off and water (1500 ml) was added. Crude 8 was extracted into ethyl acetate, dried over Na₂SO₄, distilled and purified by column chromatography on silica gel using hexane as eluant to give pure 8 (175 g, 85%) as a light yellow syrup. The structure was confirmed with NMR.

¹HNMR (CDCl₃) 1.55 (d, 3H, CH₃), 1.68 (d, 3H, CH₃), 3.62 (s, 3H, ester), 3.72 (s, 3H, ester), 3.82 (q, 1H, CH), 3.91 (q, 1H, OCH), 7.02 (s, 1H, Ar), 7.18 (d, 1H, Ar), 7.36 (d, 1H, Ar), 7.68 (m, 3H, Ar)

Example 9

6-[6-(1-Methoxycarbonyl-ethyl)-naphthalen-2-yloxy]-hexanoic acid methyl ester (9)

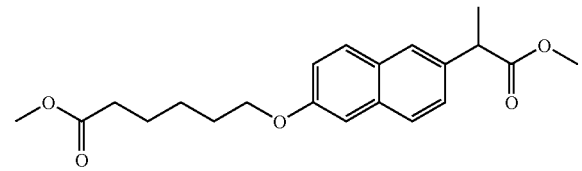

To a mixture of 2-(6-Hydroxy-naphthalen-2-yl)-propionic acid methyl ester 6 (150 g, 652 mmol), anhydrous K₂CO₃ (480 gr, 3.473 mol) and sodium iodide (22.5 grams, 150 mmol) in anhydrous acetone (2000 ml) was added methyl 6-bromohexanoate (216 g, 1.033 mol) and refluxed for 60 hours. Acetone was distilled off and water (1500 ml) was added. Crude 9 was extracted into ethyl acetate, dried over Na₂SO₄, distilled and purified by column chromatography on silica gel using hexane as eluant to give pure 2 (130 g, 55.6%) as a light yellow syrup. The structure was confirmed with NMR.

¹HNMR (CDCl₃) 1.59 (d, 3H, CH₃), 1.60 (d, 2H, CH₂), 1.75 (m, 2H, CH₂), 1.89 (m, 2H, CH₂), 2.38 (t, 2H, CH₂), 3.69

(s, 6H, ester), 3.88 (q, 1H, CH), 4.08 (t, 2H, OCH$_2$), 7.10 (m, 2H, Ar), 7.40 (d, 1H, Ar), 7.68 (m, 3H, Ar)

Example 10

{2-Methoxy-4-[(8-methyl-non-6-enoylamino)-methyl]-phenoxy}-acetic acid methyl ester (10)

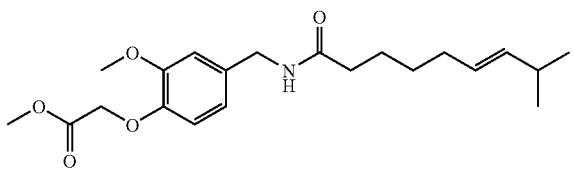

To a mixture of Capsaicin (17 g, 55.7 mmol), anhydrous K$_2$CO$_3$ (26 g, 188 mmol), sodium iodide (4.5 g, 30 mmol) and disodium phosphate (4.5 g, 32 mmol) in anhydrous acetone (425 ml) was added methyl chloroacetate (9 g, 83 mmol) and refluxed for 6 hours. Acetone was distilled off and water (150 ml) was added. Crude 10 was filtered, dried and recrystallised from toluene to give pure 10 (15 g, 71.4%) as a white power. The melting point was found to be 99.5-103.5° C. It was analyzed by HPLC and found to be 99.3% pure.

Example 11

2-{2-Methoxy-4-[(8-methyl-non-6-enoylamino)-methyl]-phenoxy}-propionic acid methyl ester (11)

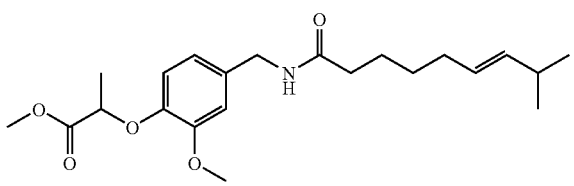

To a mixture of Capsaicin (2 g, 6.56 mmol), anhydrous K$_2$CO$_3$ (3 g, 22 mmol), and sodium iodide (2 g, 14.2 mmol) in anhydrous acetone (50 ml) was added methyl 2-chloropropionate (1.2 g, 10 mmol) and refluxed for 16 hours. Acetone was distilled off and water (15 ml) was added. Crude 11 was filtered, dried and recrystallised from a mixture of chloroform:hexane (1:5) to give pure 11 (0.8 g, 31.2%) as a white powder. The melting point was found to be 62.3-64° C.

Example 12

6-{2-Methoxy-4-[(8-methyl-non-6-enoylamino)-methyl]-phenoxy}-hexanoic acid methyl ester (12)

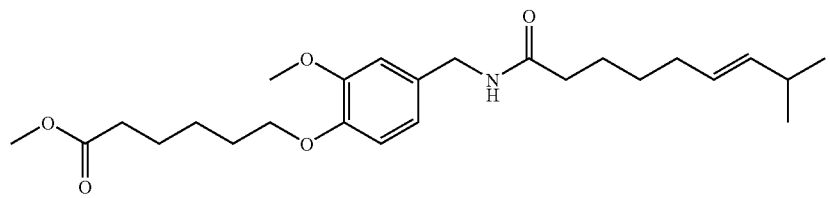

To a mixture of Capsaicin (2 g, 6.56 mmol), anhydrous K$_2$CO$_3$ (3 g, 22 mmol), sodium iodide (2 g, 13.3 mmol) and disodium phosphate (2 g, 14.2 mmol) in anhydrous acetone (50 ml) was added methyl 6-bromohexanoate (2 g, 9.6 mmol) and refluxed for 24 hours. Acetone was distilled off and water (15 ml) was added. Crude 12 was filtered, dried and purified by column chromatography on silica gel using benzene:ethyl acetate (9:1) to give pure 12 (1.5 g, 52.8%) as a pale white powder. The melting point was found to be 69.2-70.8° C.

Example 13

(4-Acetylamino-phenoxy)-acetic acid ethyl ester (13)

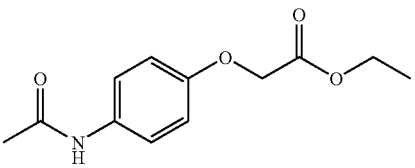

To a mixture of Paracetamol (300 g, 1.984 mol), and anhydrous K$_2$CO$_3$ (1.80 Kg, 7.814 mmol) in anhydrous acetone (3 liters) was added ethyl bromoacetate (452 gr, 2.7 mol) and refluxed for 16 hours. Acetone was distilled off and water (5 liter) was added. Crude 13 was filtered, dried and recrystallised from a mixture of toluene:hexane (1:5) to give pure 13 (377 g, 80%) as a white shining powder. The melting point was found to be 104.2-106.2° C.

Example 14

(4-Amino-phenoxy) acetic acid HCl (14)

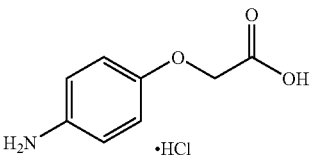

A mixture (4-Acetylamino-phenoxy)-acetic acid ethyl ester 13 (375 g, 1.582 mmol), in concentrated hydrochloric acid (9.36 liters) was refluxed for 12 hours. Excess concentrated hydrochloric acid was distilled off in vacuum and filtered hot. The mixture was cooled to 10° C., filtered and dried to give pure 14 (250 g, 77.6%) as a wheat colored powder. The melting point was found to be 224-226° C. The structure was confirmed with NMR.

¹HNMR (D₂O) 4.68 (s, 2H, OCH2), 3.65 (s, 3H, ester), 7.0 (d, 2H, Ar), 7.30 (d, 2H,Ar

Example 15

(4-Amino-phenoxy)-acetic acid methyl ester (15)

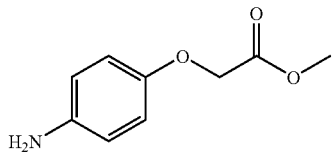

To a mixture of (4-Aminophenoxy)acetic acid HCl 14 (250 g, 1.228 mol), in methanol (5 L) was passed dry HCl gas at 10° C. for 1 hour and refluxed for 10 hours. Methanol (3.5 liters) was distilled off, ice water (1 liter) was added and the pH was adjusted to 7.5 with K₂CO₃. Crude 15 was filtered, dried and recrystallised from a mixture of chloroform:hexane (1:5) to give pure 15 (130 g, 58.5%) as a light brown powder. The melting point was found to be 65-66.8° C.

Example 16

2-(4-Acetylamino-phenoxy)-propionic acid methyl ester (16)

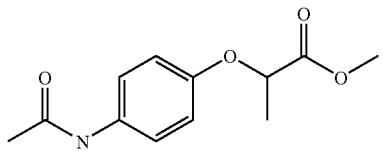

To a mixture of Paracetamol (150 grams, 992 mmol), anhydrous K₂CO₃ (540 Kg, 3.91 mol) and sodium iodide (18 g, 120 mmol) in anhydrous acetone (3 liters) was added methyl 2-chloropropionate (180 g, 1.469 mmol) and refluxed for 80 hours. Acetone was distilled off and water (3 liter) was added. Crude 16 was extracted into chloroform, dried over Na₂SO₄, distilled in hexane (750 ml), filtered and recrystallised in methanol to give pure 16 (95 g, 40.4%) as a white powder. The melting point was found to be 96.5-98.2° C. The product was tested by HPLC and found to be 99%+pure. The structure was confirmed with NMR.

¹HNMR (CDCl₃) 1.60(d, 3H, CH₃), 2.08 (s, 3H, O=C—CH₃), 3.76 (s, 3H, ester), 4.66 (q, 1H, CH), 6.72 (d, 2H, Ar), 7.32 (d, 2H, Ar), 8.04 (bs, 1H, NH)

Example 17

2-(4-Amino-phenoxy)-propionic acid (17)

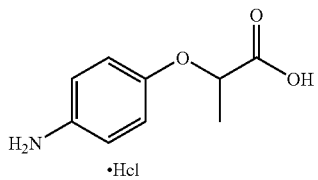

A mixture of 2-(4-Acetylaminophenoxy)propionic acid methyl ester 16 (320 grams, 1.35 mol) in concentrated hydrochloric acid (8 liters) was refluxed for 48 hours. Excess concentrated hydrochloric acid was distilled off in vacuum and filtered hot. The mixture was cooled to 10° C., filtered and dried to give pure 17 (240 g, 81.7%) as a brown powder. The melting point was found to be 175-180° C.

Example 18

2-(4-Amino-phenoxy)-propionic acid methyl ester (18)

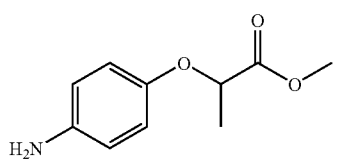

To a mixture of 2-(4-Amino-phenoxy)-propionic acid 17 (240 g, 1.103 mol), in methanol (4.8 liters) was passed dry HCl gas at 10° C. for 1 hour and refluxed for 48 hours. Methanol (2.5 liter) was distilled off, ice water (1 liter) was added and the pH was adjusted to 7.5 with K₂CO₃. Crude 18 was extracted into chloroform, washed with 5% NaHCO₃ solution, water, dried over Na₂SO₄ and distilled to give 18 (80 g, 37.2%) as a brown syrup. The structure was confirmed with NMR.

¹HNMR (CDCl₃) 1.56 (d, 3H, CH₃), 2.9 (bs, 2H,—NH₂), 3.72 (s, 3H, ester), 4.58 (q, 1H, CH), 6.53 (d, 2H, Ar), 6.68 (d, 2H, Ar)

Example 19

6-(4-Acetylamino-phenoxy)-hexanoic acid methyl ester (19)

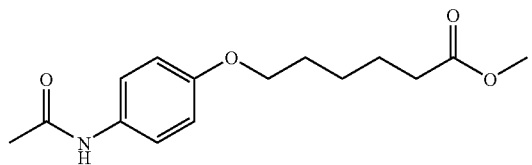

To a mixture of Paracetamol (250 g, 1.654 mol), anhydrous K₂CO₃ (800 g, 5.789 mol) and sodium iodide (17 g, 113 mmol) in anhydrous acetone (5 liters) was added methyl 6-bromohexanoate (470 g, 2.25 mol) and refluxed for 60 hours. Acetone was distilled off and water (3 liter) was added. Crude 19 was filtered, dried and recrystallised from a mixture of chloroform:hexane (1:5) to give pure 19 (195 g, 66%) as a white powder. The melting point was found to be 96.4-98.8° C. The product was tested by HPLC and found to be 99%+ pure. The structure was confirmed with NMR.

¹HNMR (CDCl₃) 1.54 (m, 2H, CH₂), 1.80 (m, 4H, CH₂), 2.14 (s, 3H, O=C—CH₂), 2.38 (t, 2H, CH₂), 3.68 (s,3H, ester), 3.92 (t, 2H, OCH₂), 6.68 (d, 2H, Ar), 7.05 (bs, 1H, NH), 7.38 (d, 2H, Ar).

Example 20

6-(4-Amino-phenoxy)-hexanoic acid Hydrochloride (20)

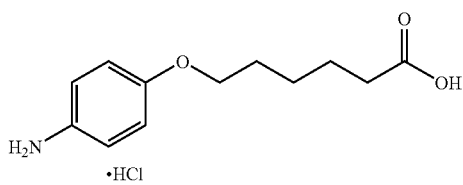

A mixture of 6-(4-Acetylaminophenoxy)hexanoic acid methyl ester 19 (290 grams, 1.04 mol) in concentrated hydrochloric acid (7.12 L) was refluxed for 48 hours. Excess concentrated hydrochloric acid was distilled off in vacuum and filtered hot. The mixture was cooled to 10° C., filtered and dried give pure 20 (150 g, 55.6%) as a brown powder. The melting point was found to be 155-160° C.

Example 21

6-(4-Amino-phenoxy)-hexanoic acid methyl ester (21)

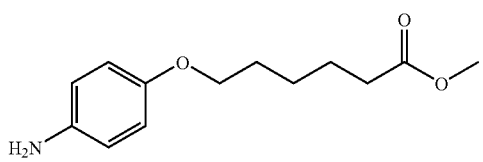

To a mixture of 6-(4-Amino-phenoxy)-hexanoic acid hydrochloride 20 (150 grams, 578 mmol) in methanol (3 liters) was passed dry HCl gas at 10° C. for 1 hour and refluxed for 48 hours. Methanol (1.5 liter) was distilled off, ice water (1 liter) was added and the pH was adjusted to 7.5 with $K_2CO_3$. Crude 21 was extracted into chloroform, washed with 5% $NaHCO_3$ solution in water, dried over $Na_2SO_4$ and distilled to give 21 (60 g, 43.8) as a thick brown syrup. The structure was confirmed with NMR.

$^1$HNMR (CDCl$_3$) 1.5 (m, 2H, CH$_2$), 1.72 (m, 4H, CH$_2$), 2.34 (t, 2H, CH$_2$), 3.66 (s, 3H, ester), 3.85 (t, 2H, OCH$_2$), 6.56 (d, 2H, Ar), 6.68 (d, 2H, Ar).

Example 22

[2-(4-Nitrophenoxy)-ethoxy]acetic acid methyl ester (22)

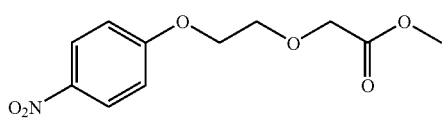

To a mixture of 4-nitrophenol (5 g, 36 mmol), anhydrous $K_2CO_3$ (20 g, 145 mmol) and sodium iodide (2 grams, 13.3 mmol) in anhydrous acetone (100 ml) was added (2-bromoethoxy) acetic acid methyl ester (11 g, 56 mmol) and refluxed for 24 hours. Acetone was distilled off and water (100 ml) was added. Crude 22 was filtered, dried and purified by column chromatography on silica gel using benzene as eluant to give pure 22 (4 g, 43.6%) as a white fluffy powder. The melting point was found to be 96-97.8° C. The structure was confirmed with IR and NMR.

$^1$HNMR (CDCl$_3$+DMSO) 3.72 (s, 3H, ester), 3.94 (t, 2H, OCH$_2$), 4.18 (s, 2H, OCH$_2$), 4.30 (t, 2H, OCH$_2$), 7.08 (d, 2H, Ar), 8.18 (d, 2H, Ar)

Example 23

[2-(4-Amino-phenoxy)-ethoxy]-acetic acid methyl ester (23)

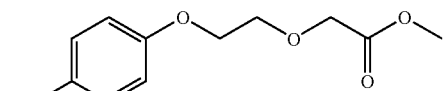

[2-(4-Nitrophenoxy)-ethoxy]acetic acid methyl ester 22 (1 g, 3.9 mmol) was dissolved in anhydrous ethyl acetate (20 ml), palladium carbon (10%, 0.1 g) added and the mixture stirred under an atmosphere of hydrogen using balloon for 30 minutes. The catalyst was filtered, the filtrate concentrated, hexane (3 ml) added, and the solid filtered to give 23 (625 mg, 70.9%) as a light brown powder. The melting point was found to be 51-52.5° C. The structure was confirmed with IR and NMR.

$^1$HNMR (CDCl$_3$) 3.04 (bs, 2H, NH$_2$), 3.72 (s, 3H, ester), 3.88 (t, 2H, OCH$_2$), 4.08 (t, 2H, OCH$_2$), 4.20 (s, 2H, OCH$_2$), 6.58 (d, 2H, Ar), 6.70 (d, 2H, Ar)

Example 24

Benzyloxy-acetic acid 4-acetylamino-phenyl ester (24)

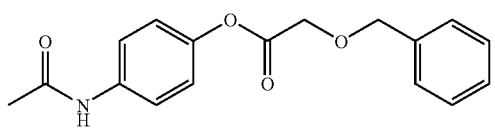

To mixture of Paracetamal (25 g, 165 mmol) and triethylamine (41.5 g, 410 mmol) in acetone (250 ml) at 10° C. was added benzyloxy acetyl chloride (40 g, 217 mmol) drop wise, followed by stirring at room temperature for 16 hours. The solids were filtered off, acetone was distilled off and water (200 ml) was added. Crude 24 was extracted into chloroform, washed with 5% Sodium bicarbonate solution (2×100 ml), water (2×100 ml), distilled and purified by column chromatography on silica gel using benzene as eluant to get pure 24 (30 g, 60.7%) as a light brown powder. M.p: 106-108.8° C.

Example 25

Hydroxy-acetic acid 4-acetylamino-phenyl ester (25)

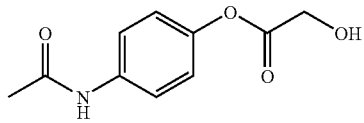

Benzyloxyacetic acid 4-acetylamino-phenyl ester 24 (15 g, 50 mmol) was dissolved in methanol (150 ml) in a pressure vessel, palladium on carbon (5%, 8 grams) added and the mixture stirred under an atmosphere of hydrogen (3 Kg) for 20 hours. The catalyst was removed by filtration and the methanol was then distilled off. The crude 25 was recrystallized from mixture of chloroform:methanol (1:4) to get pure 25 (6 g, 57.2%) as a white powder. M.p: 144-146° C.

Example 26

2-Benzyloxy-N-(4-hydroxy-phenyl)-acetamide (26)

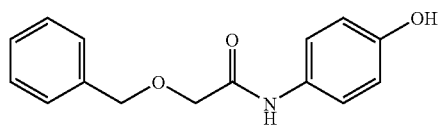

To mixture of 4-aminophenol (20 g, 183.2 mmol) and sodium bicarbonate (17 grams, 202 mmol) in acetone (150 ml) at 0° C. was added benzyloxy acetyl chloride (40 g, 216.8 mmol) drop wise, followed by stirring at room temperature for 20 hours. The solids were filtered off, and cold water (500 ml) was added. Crude 26 was extracted into chloroform, washed with 5% sodium bicarbonate solution (2×100 ml), water (2×100 ml), dried over sodium sulphate and distilled. The crude 26 was purified by column chromatography on silica gel using chloroform as eluant to get pure 26 (23 g, 48.9%) as a light orange syrup.

Example 27

2-Hydroxy-N-(4-hydroxy-phenyl)-acetamide (27)

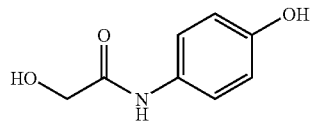

2-Benzyloxy-N-(4-hydroxy-phenyl)-acetamide 26 (18 g, 70 mmol) was dissolved in methanol (100 ml) in a pressure vessel, palladium on carbon (5%, 8 g) was added and the mixture stirred under an atmosphere of hydrogen (4 Kg) for 8 hours. The catalyst was removed by filtration and the methanol was distilled off. The crude 27 was recrystallized from a mixture of chloroform:methanol (1:5) to get pure 27 (4 grams, 34.2%) as a white shining powder.
m.p: 141-142.6° C.

Example 28

(4-Isocyanato-phenoxy)-acetic acid methyl ester (28)

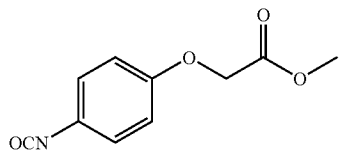

To a mixture of (4-Amino-phenoxy)-acetic acid methyl ester 15 (15 g, 82.87 mmol) and triethylamine (16.77 g, 165.73 mmol) in toluene (225 ml) under nitrogen atm. at 0° C. was added triphosgene (9 g, 30.33 mmol) in one lot. The reaction was exothermic and the temperature raised to 25° C. Later the reaction mixture was heated to 75° C. over a period of one hour and maintained at this temperature for 26 hours. The reaction mixture was then cooled to room temperature, the solids were filtered off, and the toluene was distilled off under vacuum to get crude 28, which was vacuum distilled to get pure 28 (10 g, 58.3%) as a white powder. M.p: 50-53° C.

Example 29

[4-(2-Hydroxy-ethoxycarbonylamino)-phenoxy]-acetic acid methyl ester (29)

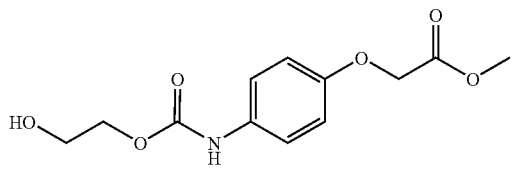

(4-Isocyanato-phenoxy)-acetic acid methyl ester 28 (15 g, 72.46 mmol) was added to ethylene glycol (30 ml) at room temperature. The reaction was exothermic and the temperature raised to 42° C. Later the reaction mixture was stirred at room temperature for 16 hours. Water (100 ml) was added and crude 29 was filtered, dried and purified by column chromatography on silica gel using chloroform as eluant to get pure 29 (16.17 g, 82.9%) as a off-white powder. M.p: 85.5-87.5° C.

Example 30

{4-[2-(4-Methoxycarbonylmethoxy-phenylcarbamoyloxy)-ethoxycarbonylamino]-phenoxy}-acetic acid methyl ester (30)

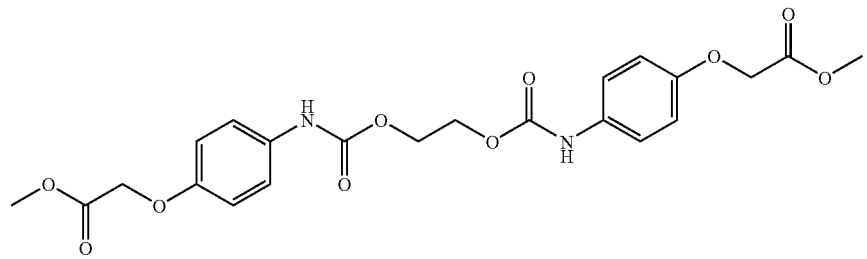

To [4-(2-Hydroxy-ethoxycarbonylamino)-phenoxy]-acetic acid methyl ester 29 (1 g, 3.72 mmol) in toluene (10 ml) was added (4-Isocyanato-phenoxy)-acetic acid methyl ester 28 (0.8 g, 3.8 mmol) at room temperature and heated to 50° C. for 20 hours. Toluene was distilled off and water (10 ml) was added. Crude 30 was extracted into chloroform, dried over sodium sulphate, distilled and purified by column chromatography on silica gel using chloroform as eluant to get pure 30 (1 g, 56.5%) as a white fluffy powder.

Example 31

Methyl (4-Nitro phenoxy) acetate (31)

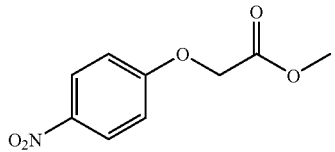

To a mixture of 4-Nitro phenol (100 g, 719 mmol) and anhydrous $K_2CO_3$ (400 g, 2.894 moles) in anhydrous acetone (950 ml) was added methyl chloroacetate (114 g, 1.050 moles) and refluxed for 12 hours. Acetone was distilled off and water (1500 ml) added. Crude 31 was filtered, dried and recrystallised from a mixture of ethyl acetate:hexane (1:5) to give pure 31 (110 g, 72.5%) as a white fluffy powder. M.p: 97-98.4° C.

Example 32

2-(4-Isocyanato-phenoxy)-propionic acid methyl ester (32)

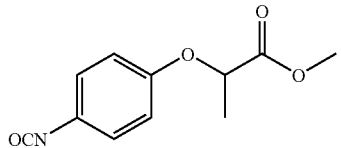

To a mixture of 2-(4-Aminophenoxy)propionic acid methyl ester 18 (15 grams, 76.9 mmol) and triethylamine (15.6 g, 154.16 mmol) in toluene (210 ml) under nitrogen atm. was added triphosgene (8.4 g, 28.3 mmol) in one lot. Later the reaction mixture was heated to 75° C. over a period of one hour and maintained at this temp. for 26 hours. The reaction mixture was cooled to room temperature, the solids were filtered off, and the toluene was distilled off under vacuum to get crude 32, which was vacuum distilled to get pure 32 (9 g, 52.9%) as a light yellow syrup.

Example 33

2-[4-(2-Hydroxy-ethoxycarbonylamino)-phenoxy]-propionic acid methyl ester (33)

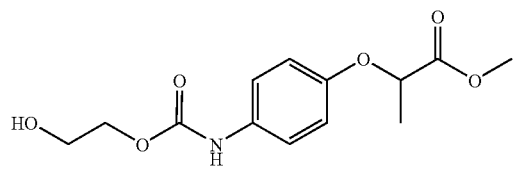

2-(4-Isocyanato-phenoxy)-propionic acid methyl ester 32 (20 g, 90.49 mmol) was added to ethylene glycol (40 ml) at room temperature. The reaction was exothermic and the temperature rose to 58° C. The mixture was allowed to cool and later stirred at room temperature for 16 hours. Water (150 ml) was added and crude 33 was extracted into chloroform, washed with water (2×50 ml), dried over sodium sulphate and distilled. Crude 33 was purified by column chromatography on silica gel using chloroform as eluant to get pure 33 (13 gr, 50.76%) as a syrup which crystallized in 48 hours as a white powder. M.p: 90.5-92.8° C.

Example 34

2-(4-{2-[4-(1-Methoxycarbonyl-ethoxy)-phenylcarbamoyloxy]-ethoxycarbonylamino}-phenoxy)-propionic acid methyl ester (34)

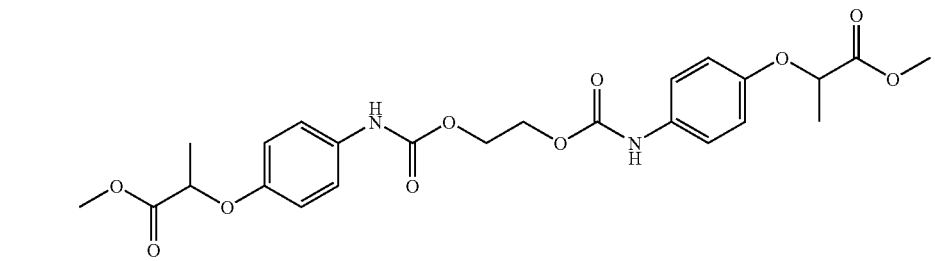

To 2-[4-(2-Hydroxyethoxycarbonylamino)phenoxy]propionic acid methyl ester 33 (5 g, 17.66 mmol) in toluene (50 ml) was added 2-(4-Isocyanato-phenoxy)-propionic acid methyl ester 32 (3.9 g, 17.64 mmol) at room temperature and heated to 60° C. for 30 hours. Toluene was distilled off and water (50 ml) was added. The solids were filtered and dried to give crude 34, which was purified by column chromatography on silica gel using chloroform as eluant to get pure 34 (5.5 g, 61.8%) as a white powder. M.p: 98-100° C.

Example 35

2-(4-Nitro-phenoxy)-propionic acid methyl ester (35)

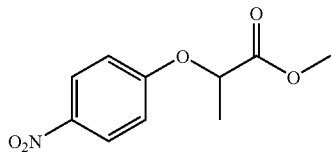

To a mixture of 4-nitrophenol (200 g, 1.439 mol), anhydrous $K_2CO_3$ (800 g, 5.789 mol) and sodium iodide (10 g, 66.7 mmol) in anhydrous acetone (2.75 L) was added methyl 2-chloro propionate (264 g, 2.154 mol) and refluxed for 20 hours. The acetone was distilled off and water (3 L) was added. Crude 35 was filtered, dried and recrystallised from a mixture of ethyl acetate:hexane (1:5) to give pure 35 (100 g, 31%) as a white fluffy powder. M.p: 83-84° C.

Example 36

6-(4-Isocyanato-phenoxy)-hexanoic acid methyl ester (36)

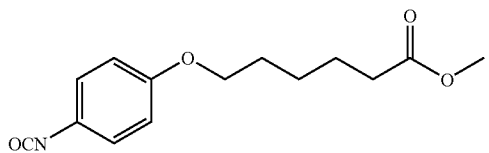

To a mixture of 6-(4-amino-phenoxy) hexanoic acid methyl ester 21 (26 grams, 109.7 mmol) and triethylamine (29.2 g, 288.56 mmol) in toluene (390 ml) under nitrogen atm. was added triphosgene (15.6 grams, 52.56 mmol) in one lot. The reaction was exothermic and the internal temperature rose to 60° C. Later, the reaction mixture was heated to 75° C. over a period of one hour and maintained at this temperature for 26 hours. The reaction mixture was cooled to room temperature, the solids were filtered, and the toluene was distilled off under vacuum to get crude 36, which was vacuum distilled to get pure 36 (10 g, 34.7%). M.p: 47-50° C.

Example 37

6-[4-(2-Hydroxy-ethoxycarbonylamino)-phenoxy]-hexanoic acid methyl ester (37)

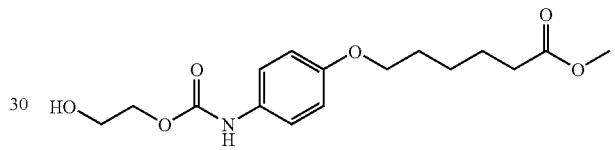

6-(4-Isocyanato-phenoxy)-hexanoic acid methyl ester 36 (15 g, 57 mmol) was added to ethylene glycol (50 ml) at room temperature. The reaction was exothermic and the temperature rose to 46° C. The reaction mixture was allowed to cool to room temperature and later stirred at room temperature for 16 hours. Water (150 ml) was added and crude 37 was filtered, dried and recrystallised from toluene to get pure 37 (12 g, 84%) as a white powder. M.p: 69.5-71.5° C.

Example 38

6-(4-{2-[4-(5-Methoxycarbonyl-pentyloxy)-phenyl-carbamoyloxy]-ethoxycarbonylamino}-phenoxy)-hexanoic acid methyl ester (38)

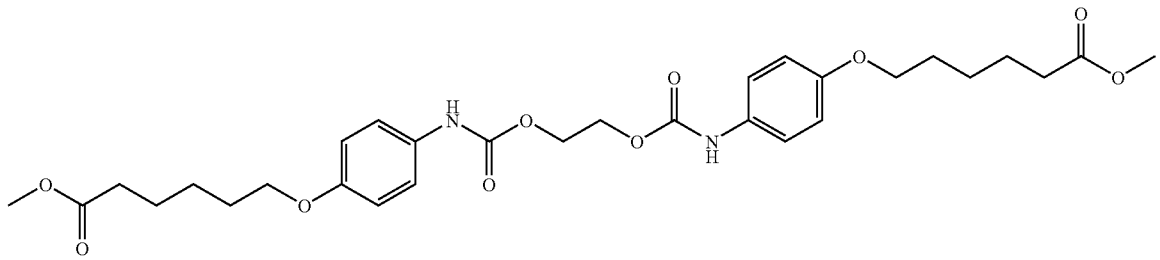

To a mixture of 6-[4-(2-Hydroxyethoxycarbonylamino) phenoxy]hexanoic acid methyl ester 37 (5 g, 15.38 mmol) in toluene (50 ml) was added 6-(4-Isocyanatophenoxy) hexanoic acid methyl ester 36 (4 g, 15.2 mmol) at room temperature and heated to 60° C. for 2 hours. Toluene was distilled off and water (50 ml) was added. The solid was filtered and dried to give crude 38, which was purified by column chromatography on silica gel using chloroform as eluant to get pure 38 (8.5 g, 94%) as a white powder. M.p: 118-120.5° C.

Example 39

6-(4-Nitro-phenoxy)-hexanoic acid methyl ester (39)

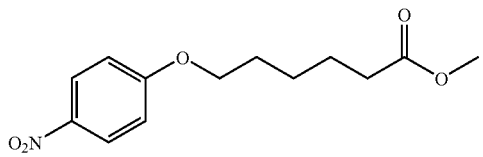

To a mixture of 4-nitrophenol (150 g, 1.079 moles), potassium carbonate (600 g, 4.341 moles) and sodium iodide (10 g, 66.7 mmol) in anhydrous acetone (2.1 L) was added methyl 6-bromohexanoate (156 g, 746.41 mmol) and heated to reflux for 48 hours. Acetone was distilled off and water (2 L) was added. Crude 39 was filtered, dried and recrystallised from a mixture of ethyl acetate:hexane (1:6) to get pure 39 (130 g, 45.1%) as a white powder. M.p: 84.5.5-86.6° C.

Example 40

(4-Nitro phenoxy) acetic acid (40)

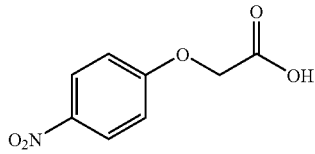

A mixture of methyl (4-nitrophenoxy)acetate 31 (100 g, 474 mmol) and concentrated HCl (1000 ml) was refluxed for 8 hours. The reaction mass was cooled to room temp. Crude 40 was filtered, dried and recrystallised from a mixture of ethyl acetate:hexane (1:5) to give pure 40 (86 g, 92.1%) as a white shining powder. M.p: 186-188.5° C.

Example 41

(4-Nitro-phenoxy)-acetic acid-2-hydroxy-ethyl ester (41)

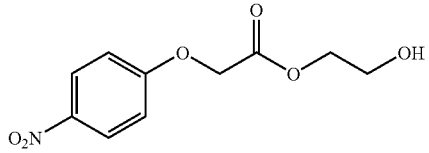

To a mixture of (4-nitrophenoxy)acetic acid 40 (100 g, 507 mmol) and ethylene glycol (300 ml) was passed dry HCl gas for 1 hr. During HCl gas bubbling the temperature rose to 60° C. The crude reaction mass was poured onto ice (2 Kg). Crude 41 was filtered, dried and purified by column chromatography on silica gel using hexane:ethyl acetate (95:5) to give pure 41 (70 g, 57.4%) as a white powder. M.p: 73.5-75.5° C.

$^1$HNMR (CDCl$_3$) δ 3.70 (m, 2H, CH$_2$), 4.28 (m, 2H,

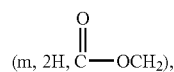

4.56 (6m, 1H, OH), 4.80 (s, 2H, OCH$_2$), 7.00 (d, 2H, Ar), 8.16 (d, 2H, Ar)

Example 42

(4-Nitro-phenoxy)-acetic acid-2-[2-(4-nitro-phenoxy)-acetoxy]-ethyl ester (42)

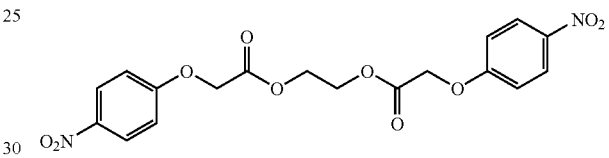

To a mixture of (4-nitrophenoxy)acetic acid 40 (80 g, 406 mmol) and (4-nitro-phenoxy)acetic acid-2-hydroxyethyl ester 41 (80 g, 332 mmol) in anhydrous dichloromethane (2 L) under nitrogen atm. was added a solution of 1,3-dicyclohexyl carbodiimide (128 g, 620 mmol) in anhydrous dichloromethane (750 ml) drop wise. The reaction mixture was stirred at room temperature for 8 hours. The solids were filtered off and dichloromethane distilled off to get crude 42. The crude 42 was purified by column chromatography on silica gel using hexane:ethyl acetate (95:5) to get pure 42 (75 g, 54%) as a white powder. M.p: 138-139° C.

Example 43

(4-Amino-phenoxy)-acetic acid-2-[2-(4-amino-phenoxy)-acetoxy]-ethyl ester (43)

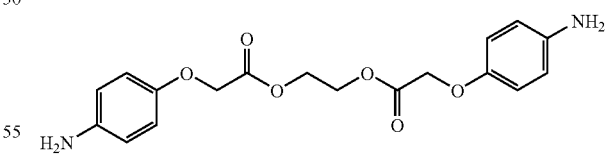

(4-nitro-phenoxy)-acetic acid-2-[2-(4-nitrophenoxy) acetoxy]ethyl ester 42 (100 g, 238 mmol) was dissolved in dry dimethylformamide (500 ml) in a pressure vessel, palladium on carbon (5%, 22 g) added, and the mixture stirred under an atmosphere of hydrogen (4 Kg) for 6 hours. The catalyst was removed by filtration and ice water (2.5 L) was added to the filtrate. Crude 43 was filtered off, dried and recrystallised in a mixture of methanol:chloroform (1:1) to give pure 43 (65 g, 78%) as a light brown shining powder. M.p: 124-125.8° C.

$^1$HNMR (CDCl$_3$) δ 4.40

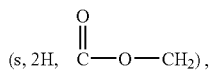

4.50 (s, 2H, OCH$_2$), 6.54 (d, 2H, Ar), 6.70 (d, 2H, Ar), 7.26 (s, 2H, —NH$_2$)

Example 44

(4-Isocyanatophenoxy)acetic acid-2-[2-(4-isocyanatophenoxy)acetoxy]ethyl ester (44)

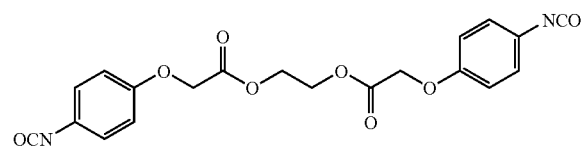

(4-Aminophenoxy)acetic acid 2-[2-(4-aminophenoxy)acetoxy]ethyl ester 43 (5 g, 14.3 mmol) was dissolved in dry dioxane (80 ml) under nitrogen atm. and cooled to below 20° C. A solution of triphosgene (7 g, 23.6 mmol) in dry dioxane (20 ml) was added drop wise. The mixture was heated slowly to 75-80° C. and maintained for 2½ hours. The condenser was then arranged for distillation and solvent removed by distillation at atmospheric pressure until the volume of the reaction mixture was reduced to approximately one third. Fresh dry dioxane (50 ml) was added and the solvents were distilled off under vacuum. The residue was re-evaporated two times from dry dioxane to give crude 44. Crude 44 was recrystallised from a mixture of toluene:hexane (1:3) to give pure 44 (2.6 g, 44.2%) as a white powder. M.p: 96-98° C.

$^1$HNMR (CDCl$_3$) δ 4.45

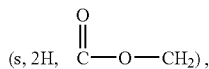

4.62 (s, 2H, OCH$_2$), 6.85 (d, 2H, Ar), 7.04 (s, 2H, Ar). IR: 2274.3 Cm$^{-1}$

Example 45

[4-(2-Hydroxy-ethoxycarbonylamino)-phenoxy]-acetic acid 2-{2-[4-(2-hydroxy-ethoxy carbonyl amino)-phenoxy]-acetoxy}-ethyl ester (45)

(4-Isocyanatophenoxy)acetic acid-2-[2-(4-isocyanatophenoxy)acetoxy]ethyl ester 44 (0.5 g, 1.21 mmol) was added to ethylene glycol (2.5 ml) at room temperature and further stirred for 17 hrs. Water (10 ml) was added, and the solid was filtered, dried and recrystallised from methanol to get pure 45 (0.4 g, 61.5%) as a white powder. M.p: 158-161° C.

Example 46

(4-Amino-phenoxy)-acetic acid 2-hydroxy-ethyl ester (46)

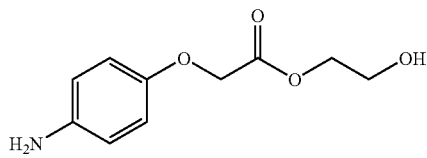

(4-Aminophenoxy)acetic acid methyl ester 41 (1 g, 4.15 mmol) was dissolved in ethyl acetate in a pressure vessel, palladium on carbon (5%, 0.5 g) was added and the mixture was stirred under an atmosphere of hydrogen (0.5 Kg) for one hour. The catalyst was removed by filtration, ethyl acetate was distilled off and hexane was added. The solid product was filtered and dried to give pure 46 (0.2 g, 22.8%) as a brown powder. M.p: 104-106.3° C.

Example 47

2-(4-Nitro-phenoxy)-propionic acid (47)

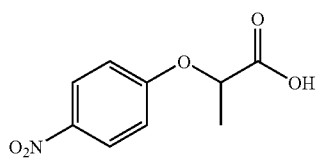

A mixture of 2-(4-nitrophenoxy)propionic acid methyl ester 35 (50 g) and concentrated HCl (500 ml) was refluxed for 8 hours. The reaction mass was cooled to room temp. Crude 47 was filtered, dried and recrystallised from a mixture of ethyl acetate:hexane (1:5) to give pure 47 (40 g, 85.3%) as a white powder. M.p: 139-141° C.

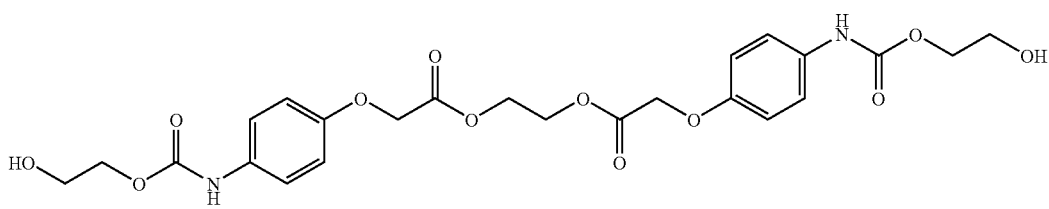

Example 48

2-(4-Nitro-phenoxy)-propionic acid 2-hydroxy-ethyl ester (48)

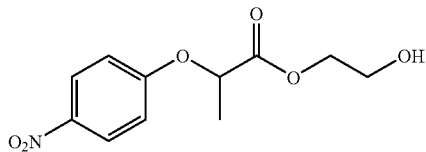

To a mixture of 2-(4-Nitro-phenoxy)-propionic acid 47 (45 g, 213 mol) and ethylene glycol (135 ml) was passed dry HCl gas for 1½ hours. During HCl gas bubbling the temp. rose to 60° C. The crude reaction mass was poured onto cold water (600 ml). Crude 48 was extracted into chloroform, dried over $Na_2SO_4$, distilled and purified by column chromatography on silica gel using hexane as eluant to give pure 48 (28 g, 56.8%) as a syrup.

$^1$HNMR (CDCl$_3$) δ 1.62(d, 3H, CH$_3$), 2.64 (bs, 1H, OH), 3.68 (m, 2H, CH$_2$), 4.20 (m, 2H, CH$_2$), 4.82 (q, 1H, OCH), 6.85(d, 2H, Ar), 8.05(d, 2H, Ar)

Example 49

2-(4-Nitrophenoxy)propionic acid 2-[2-(4-nitrophenoxy)propionyloxy]ethyl ester (49)

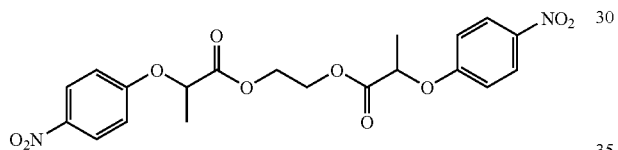

To a mixture of 2-(4-nitrophenoxy) propionic acid 47 (25 grams, 118.5 mmol) and 2-(4-nitrophenoxy)propionic acid 2-hydroxyethyl ester 48 (25 grams, 108 mmol) in anhydrous dichloromethane (625 ml) under nitrogen atm. was added dropwise a solution of 1,3-dicyclohexyl carbodiimide (40 g, 194 mmol) in anhydrous dichloro-methane (250 ml). The reaction mixture was stirred at room temperature for 8 hours. The solids were filtered off and dichloromethane distilled off to get crude 49. The crude 49 was purified by column chromatography on silica gel using hexane as eluant to get pure 49 (17 g, 35.1%) as a white powder.

$^1$HNMR (DMSO) δ 1.50 (d, 3H, CH$_3$), 4.36

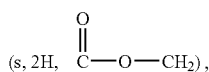

(s, 2H, C—O—CH$_2$), 5.22 (q, 1H, OCH), 7.08 (d, 2H, Ar), 6.16 (d, 2H, Ar)
m.p: 117.5-120.5° C.

Example 50

2-(4-Aminophenoxy)propionic acid-2-[2-(4-aminophenoxy)propionyloxy]ethyl ester (50)

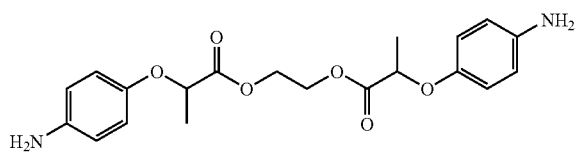

2-(4-nitrophenoxy)propionic acid-2-[2-(4-nitrophenoxy)propionyloxy]ethyl ester 49 (50 g, 89.3 mmol) was dissolved in dry dimethylformamide (400 ml) in a pressure vessel, palladium on carbon (5%, 12.5 g) added, and the mixture stirred under an atm. of hydrogen (4 Kg) for 4 hours. The catalyst was removed by filtration and ice water (3 L) was added to the filtrate. Crude 50 was extracted into ethyl acetate, dried over Na$_2$SO$_4$, distilled and purified by column chromatography on silica gel using chloroform as eluant to give pure 50 (25 g, 58%) as a syrup.

$^1$HNMR (CDCl$_3$) δ 1.52 (d, 3H, CH$_3$), 3.30 (bs, 2H, NH$_2$), 4.30 (s, 2H,

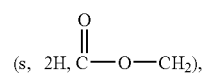

(s, 2H, C—O—CH$_2$), 4.56 (q, 1H, OCH), 6.50 (d, 2H, Ar), 6.66 (d, 2H, Ar)

Example 51

2-(4-Isocyanatophenoxy)propionic acid-2-[2-(4-isocyanatophenoxy)propionyloxy]ethyl ester (51)

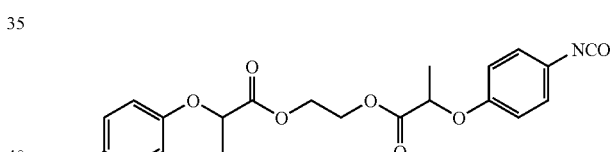

2-(4-Aminophenoxy)propionic acid-2-[2-(4-aminophenoxy)propionyloxy]ethyl ester 50 (5.3 g, 13.6 mmol) was dissolved in dry dioxane (80 ml) under nitrogen atm. and cooled below 20° C. A solution of triphosgene (7 g, 23.6 mmol) in dry dioxane (20 ml) was added dropwise. The mixture was heated slowly to 75-80° C. and maintained for 2½ hours. The condenser was then arranged for distillation and solvent removed by distillation at atmospheric pressure until the volume of reaction mixture was reduced to approximately one third. Fresh dry dioxane (50 ml) was added and the solvents were distilled off under vacuum. The residue was re-evaporated two times from dry dioxane to give pure 51 (4 g, 66.5%) as a light brown liquid.

$^1$HNMR (CDCl$_3$) δ 1.60 (d, 3H, CH$_3$), 4.41

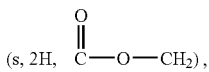

(s, 2H, C—O—CH$_2$), 4.68 (q, 1H, OCH), 6.84 (d, 2H, Ar), 7.00 (d, 2H, Ar)

Example 52

2-[4-(2-Hydroxyethoxycarbonylamino)phenoxy]propionic acid-2-{2-[4-(2-hydroxy-ethoxycarbonylamino)phenoxy]propionyloxy}ethyl ester (52)

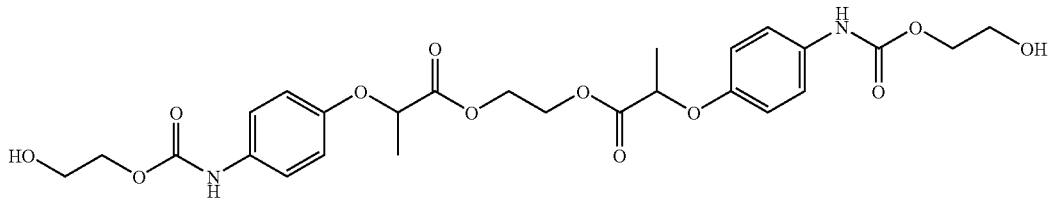

2-(4-Isocyanatophenoxy)propionic acid-2-[2-(4-isocyanatophenoxy)propionyloxy]ethyl ester 51 (0.5 g, 1.1 mmol) was added to ethylene glycol (2.5 ml) at room temperature and further stirred for 6 hours. Water (10 ml) was added, and the mixture was extracted into ethyl acetate, dried over sodium sulphate, and distilled to get crude 52, which was purified by column chromatography on silica gel using hexane:ethyl acetate (1:1) to get pure 52 (0.1 g, 15.6%).

Example 53

6-(4-Nitrophenoxy)-hexanoic acid (53)

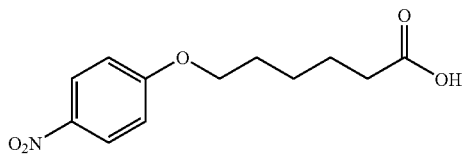

A mixture of 6-(4-nitrophenoxy) hexanoic acid methyl ester 39 (125 g, 468.16 mmol) and concentrated HCl (1250 ml) was refluxed for 16 hours. The reaction mixture was cooled to room temperature, filtered, dried and recrystallised from a mixture of ethyl acetate:hexane (1:6) to get pure 53 (95 g, 80.2%) as a white powder. M.p: 104-107° C.

Example 54

6-(4-Nitrophenoxy)hexanoic acid 2-hydroxyethyl ester (54)

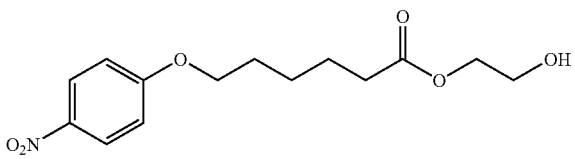

To a mixture of 6-(4-nitrophenoxy)hexanoic acid 53 (50 g, 197.62 mmol) and ethylene glycol(200 ml) was passed dry HCl gas for one hr. During HCl gas bubbling the temp. rose to 60° C. The crude reaction mass was poured onto ice (1 Kg), extracted into ethyl acetate, washed with water (2×250 ml), dried over sodium sulphate and distilled to get crude 54, which was purified by column chromatography on silica gel using benzene as eluant to get pure 54 (46 g, 78.3%) as a light yellow syrup.

Example 55

2-(4-Nitro-phenoxy)-propionic acid 2-[2-(4-nitrophenoxy)-acetoxy]-ethyl ester (55)

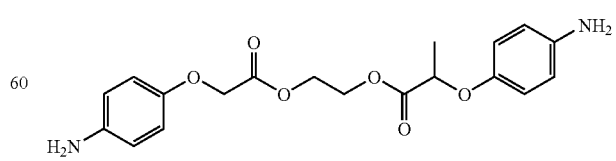

To a mixture of 4-nitrophenoxyacetic acid-2-hydroxyethyl ester 41 (100 g, 410 mmol) and 2-(4-nitrophenoxy)propionic acid 47 (95 g, 450 mmol ) in anhydrous dichloro-methane (1000 ml) under nitrogen atm. was added a solution of 1,3-dicyclohexylcarbodiimide (240 g, 1160 mmol) in anhydrous dichloromethane (600 ml) dropwise. The reaction mixture was stirred at room temperature for 12 hrs. The solids were filtered off and dichloromethane distilled off to get crude 55. The crude 55 was purified by column chromatography on silica gel using benzene as eluant to give pure 55 (53 g, 29%) as a yellow low melting solid.

$^1$HNMR (CDCl$_3$) δ 1.66 (d, 3H, CH$_3$), 4.40 (m, 4H, OCH$_2$), 4.58 (s, 2H, OCH$_2$), 4.81 (q, 1H, OCH), 6.92 (m, 4H, Ar), 8.16 (m, 4H, Ar)

Example 56

2-(4-Aminophenoxy)propionic acid-2-[2-(4-aminophenoxy)acetoxy]ethyl ester (56)

2-(4-nitrophenoxy)propionic acid-2-[2-(4-nitrophenoxy)acetoxy]ethyl ester 55 (20 g, 50 mmol) was dissolved in dry dimethylformamide (150 ml) in a pressure vessel, palladium on carbon (5%, 5 g) added, and the mixture stirred under a hydrogen atm. (4 Kg) for 3 hrs. The catalyst was removed by filtration and ice water (1 L) was added to the filtrate. Crude 56 was extracted into ethyl acetate, dried over $Na_2SO_4$, distilled and purified by column chromatography on silica gel using chloroform:ethyl acetate (8:2) to give pure 56 (10 g, 58%) as a dark brown syrup.

$^1$HNMR ($CDCl_3$) δ 1.5 (d, 3H, $CH_3$) 4.30 (s, 4H, $OCH_2$), 4.46 (s, 2H, $OCH_2$), 4.56 (q, 1H, OCH), 6.50 (m, 4H, Ar), 6.62 (m, 4H, Ar). IR: 3363.9 $Cm^{-1}$

Example 57

2-(4-Isocyanatophenoxy)propionic acid-2-[2-(4-isocyanatophenoxy)acetoxy]ethyl ester (57)

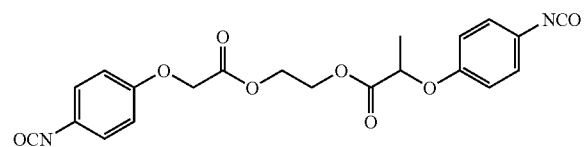

2-(4-Aminophenoxy)propionic acid-2-[2-(4-aminophenoxy)acetoxy]ethyl ester 56 (5.2 g, 13.9 mmol) was dissolved in dry dioxane (80 ml) under nitrogen atm. and cooled below 20° C. A solution of triphosgene (7 g, 23.6 mmol) in dry dioxane (20 ml) was added dropwise. The mixture was heated slowly to 75-80° C. and maintained for 3 hrs. The condenser was arranged for distillation and solvent removed by distillation at one atm. until the volume of the reaction mixture was reduced to approx. one third. Fresh dry dioxane (50 ml) was added and solvents distilled off under vacuum. The residue was re-evaporated twice from dry dioxane to give 57 (2.2 g, 37.2%) as a light yellow syrup.

IR: 2270 $Cm^{-1}$. $^1$HNMR ($CDCl_3$) δ 1.62 (d, 3H, $CH_3$) 4.40 (m, 4H, $OCH_2$), 4.52 (s, 2H, $OCH_2$), 4.72 (q, 1H, OCH), 6.80 (m, 4H, Ar), 7.00 (m, 4H, Ar)

Example 58

2-[4-(2-Hydroxyethoxycarbonylamino)phenoxy] propionic acid-2-{2-[4-(2-hydroxyethoxycarbonylamino)phenoxy]acetoxy}ethyl ester (58)

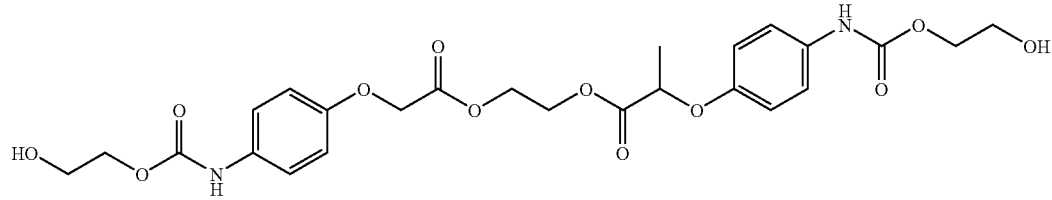

2-(4-Isocyanatophenoxy)propionic acid-2-[2-(4-isocyanatophenoxy)acetoxy]ethyl ester 57 (0.5 g, 1.17 mmol) was added to a solution of ethylene glycol (2.5 ml) in tetrahydrofuran (5 ml) at room temperature and further stirred for 3 hrs. Tetrahydrofuran was distilled off under vacuum and water (10 ml) was added. Crude 58 was extracted into ethyl acetate, washed with water (2×5ml), dried over sodium sulphate and distilled. Crude 58 was purified by column chromatography on silica gel using chloroform at eluant to get pure 58 (0.1 g, 15.6%) as a light yellow syrup.

Example 59

[2-(4-Nitrophenoxy)ethoxy]acetic acid methyl ester (59)

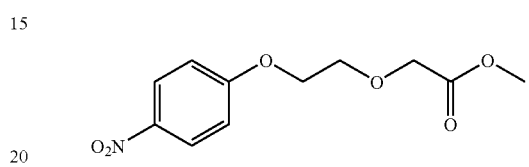

To a mixture of 4-nitrophenol (5 g, 36 mmol), anhydrous $K_2CO_3$ (20 g, 145 mmol) and sodium iodide (2 grams, 13.3 mmol) in anhydrous acetone (100 ml) was added (2-bromoethoxy)acetic acid methyl ester (11 g, 56 mmol) and refluxed for 24 hours. Acetone was distilled off and water (100 ml) was added. Crude 59 was filtered, dried and purified by column chromatography on silica gel using benzene as eluant to give pure 59 (4 g, 43.6%) as a white fluffy powder. M.p: 96-97.8° C.

$^1$HNMR ($CDCl_3$+DMSO) δ 3.72 (s, 3H, ester), 3.94 (t, 2H, $OCH_2$), 4.18 (s, 2H, $OCH_2$), 4.30 (t, 2H, $OCH_2$), 7.08 (d, 2H, Ar), 8.18 (d, 2H, Ar)

Example 60

2-(4-Aminophenoxy)ethoxyacetic acid methyl ester (60)

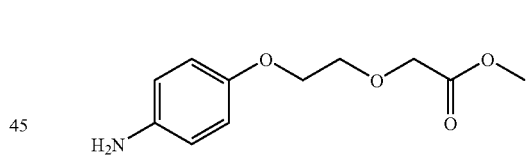

2-(4-nitrophenoxy)ethoxyacetic acid methyl ester 59 (1 g, 3.9 mmol) was dissolved in anhydrous ethyl acetate (20 ml), palladium carbon (10%, 0.1 g) added and the mixture stirred under a hydrogen atm. using a balloon for 30 min. Catalyst was filtered, filtrate concentrated, hexane (3 ml) added, and the solid filtered to give 60 (625 mg, 70.9%) as a light brown powder. M.p: 51-52.5° C.

¹HNMR (CDCl₃) δ 3.04 (bs, 2H, NH₂), 3.72 (s, 3H, ester), 3.88 (t, 2H, OCH₂), 4.08 (t, 2H, OCH₂), 4.20 (s, 2H, OCH₂), 6.58 (d, 2H, Ar), 6.70 (d, 2H, Ar)

Example 61

4-Nitrophenoxyacetic acid methoxycarbonyl methyl ester (61)

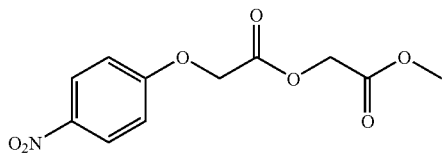

To a mixture of 4-nitrophenoxyacetic acid 40 (150 g, 761.4 mmol) and triethylamine (85 g, 840 mmol) in acetone (750 ml) was added methylchloroacetate (91.6 grams, 844 mmol) dropwise and then stirred under reflux for 8 hrs. Solids were filtered off and poured onto cold 5% sodium bicarbonate solution (4 L). Crude 61 was filtered, dried and recrystallised from chloroform:hexane (1:6) to get pure 61 (186 g, 90.8%) as a white powder. M.p: 88-90° C.

¹H NMR (CDCl₃) δ 3.80 (s, 3H, ester), 4.75 (s, 2H, OCH₂), 4.88 (s, 2H, OCH₂), 7.02 (d, 2H, Ar), 8.22 (d, 2H, Ar)

Example 62

4-Aminophenoxyacetic acid methoxycarbonyl methyl ester (62)

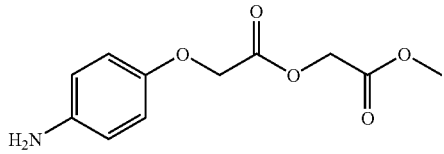

4-Nitrophenoxyacetic acid methoxycarbonyl methyl ester 61 (20 g, 74.3 mmol) was dissolved in dimethylformamide (100 ml) in a pressure vessel, palladium on carbon (5%, 8 g) added, and the mixture stirred under a hydrogen atm. (4 Kg) for 2 hrs. Catalyst was removed by filtration and ice water (400 ml) added to the filtrate. Crude 62 was extracted into ethyl acetate, dried over Na₂SO₄, distilled, and recrystallised from chloroform:hexane (1:6) to get pure 62 (13 g, 73%) as a light brown shining powder. M.p: 76.5-78.5° C.

¹H NMR (CDCl₃) δ 3.32 (bs, 2H, NH₂), 3.76 (s, 3H, ester), 4.70 (s, 2H, OCH₂), 4.74 (s, 2H, OCH₂), 6.60 (d, 2H, Ar), 6.74 (d, 2H, Ar)

Example 63

(4-Cyanatophenoxy)acetic acid methoxycarbonyl methyl ester (63)

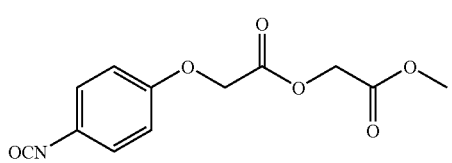

(4-Aminophenoxy)acetic acid methoxycarbonyl methyl ester 62 (10 g, 41.84 mmol) was dissolved in dry dioxane (200 ml) under nitrogen atm. and cooled below 20° C. A solution of triphosgene (10.5 g, 35.38 mmol) in dry dioxane (50 ml) was added drop-wise. The mixture was heated slowly to 70-75° C. and maintained for 2½ hours. The condenser was then arranged for distillation and the solvent removed by distillation at atmospheric pressure until the volume of the reaction mixture was reduced to approx. one third. Fresh dry dioxane (125 ml) was added and the solvents were distilled off under vacuum. The residue was re-evaporated twice from dry dioxane to give pure 63 (10 g, 90.2%) as a liquid.

IR: 2275.6 cm⁻¹. ¹H NMR (CDCl₃) δ 3.80 (s, 3H, ester), 4.74 (s, 4H, CH₂×2), 6.88 (d, 2H, Ar), 7.06 (d, 2H, Ar)

Example 64

4-(2-Hydroxyethoxycarbonylamino)phenoxyacetic acid methoxycarbonyl methyl ester (64)

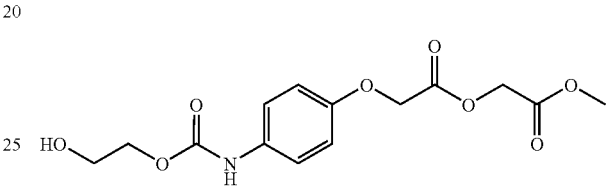

Ethylene glycol (30 ml) was added to a solution of 4-cyanatophenoxyacetic acid methoxycarbonyl methyl ester 63 (5 g, 18.85 mmol) in dry tetrahydrofuran(20 ml) and stirred at room temperature for 30 min. The reaction mixture was poured onto ice water (100 ml) and crude 64 was extracted into ethyl acetate, dried over sodium sulphate and distilled. Crude 64 was purified by column chromatography on silica gel using chloroform as eluant to get pure 64 (2 g, 32.4%). M.p: 79-82° C.

¹H NMR (CDCl₃) δ 3.76 (s, 3H, ester), 3.80 (t, 2H, CH₂), 4.25 (m, 2H, CH₂), 4.70 (s, 2H, CH₂), 4.72(s, 2H, CH₂), 6.84 (d, 2H, Ar), 7.02 (s, 1H, NH), 7.26 (d, 2H, Ar)

Example 65

(4-Acetylaminophenoxy)acetic acid methoxycarbonyl methyl ester (65)

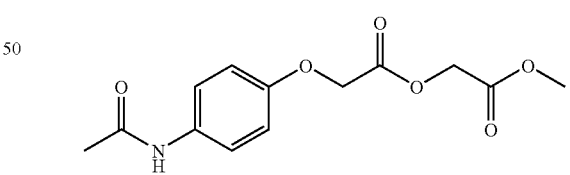

Acetyl chloride was added dropwise to a mixture of 4-aminophenoxyacetic acid methoxycarbonyl methyl ester 62 (3 g, 12.5 mmol) and triethylamine (3.8 g, 37.5 mmol) in acetone (30 ml) at 0° C. and stirred at room temperature for 12 hrs. The solids were filtered, the acetone distilled off and cold water (15 ml) was added. Crude 65 was extracted into chloroform, washed with 5% sodium bicarbonate solution (2×5 ml), water (2×5 ml), dried over sodium sulphate and distilled. Crude 65 was recrystallised from a mixture of chloroform:hexane (1:6) to give pure 65 (3 g, 85%) as an off-white powder. M.p: 98.6-101.5° C.

¹H NMR (CDCl₃) δ 2.20 (s, 3H, COCH₃), 3.78 (s, 3H, ester), 4.70 (s, 4H, CH₂×2), 6.82 (d, 2H, Ar), 7.18 (s, 1H, NH), 7.35 (d, 2H, Ar)

Example 66

4-(2-Benzyloxyacetylamino)phenoxyacetic acid methyl ester (66)

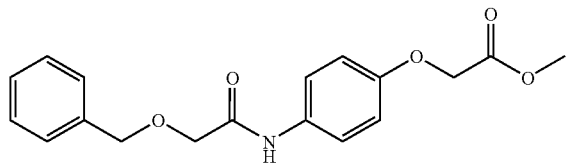

To a mixture of 4-aminophenoxyacetic acid methyl ester 15 (20 g, 110.5 mmol) and benzyloxyacetic acid (20.4 g, 123 mmol) in anhydrous dichloromethane (200 ml) under nitrogen atm. was added dropwise a solution of 1,3-dicyclohexylcarbodiimide (63.2 g, 306 mmol) in anhydrous dichloromethane (80 ml). The reaction mixture was stirred at room temp. for 12 hrs. The solids were filtered off, the dichloromethane solution was washed with 5% sodium bicarbonate solution (100 ml), water (100 ml), dried over sodium sulphate, and distilled to get crude 66. The crude 66 was purified by column chromatography on silica gel using benzene as eluant to get pure 66 (25 g, 68.9%) as a white powder. M.p: 76-77.5° C.

¹H NMR (CDCl₃) δ 3.82 (s, 3H, ester), 4.10 (s, 2H, CH₂), 4.62 (s, 2H, CH₂), 4.66 (s, 2H, CH₂), 6.88 (d, 2H, Ar), 7.38 (m, 5H, Ar), 7.46 (d, 2H, Ar), 8.24 (bs, 1H, NH)

Example 67

4-(2-Hydroxyacetylamino)phenoxyacetic acid methyl ester (67)

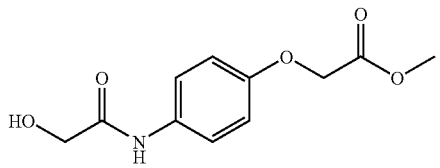

4-(2-Benzyloxyacetylamino)-phenoxyacetic acid methyl ester 66 (25 g, 76 mmol) was dissolved in methanol (450 ml) in a pressure vessel, palladium on carbon (5%, 10 g) added and the mixture stirred under a hydrogen atm. (2 Kg) for 5 hrs. Catalyst was removed by filtration and methanol distilled off. Crude 67 was recrystallised in chloroform:hexane (1:6) to give pure 67 (14 g) as a white powder. M.p: 147.5-150° C.

¹H NMR (CDCl₃+DMSO-d₆): δ 3.74 (s, 3H, ester), 3.96 (d, 2H, CH₂OH), 4.64 (s, 2H, OCH₂), 5.48 (t, 1H, OH), 6.80 (d, 2H, Ar), 7.54 (d, 2H, Ar) 9.2 (bs, 1H, NH)

Example 68

2-[4-(2-Benzyloxyacetylamino)phenoxy]propionic acid methyl ester (68)

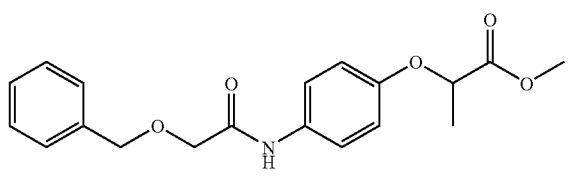

Benzyloxyacetyl chloride (28 g, 152 mmol) was added dropwise to a mixture of 2-(4-aminophenoxy)propionic acid methyl ester 18 (20 g, 102.5 mmol) and triethylamine (23 ml, 165 mmol) in acetone (120 ml) at 0° C. and stirred at room temperature for 12 hrs. Solids were filtered off, acetone distilled off and water (100 ml) added. Crude 68 was extracted into chloroform, washed with 5% sodium bicarbonate (2×100 ml), water (200 ml), dried over sodium sulphate and distilled. Crude 68 was purified by column chromatography on silica gel using benzene as eluant to get pure 68 (21 g, 59.8%) as a light brown powder. M.p: 67-70° C.

¹H NMR (CDCl₃) δ 1.60 (d, 3H, CH₃), 3.72 (s, 3H, ester), 4.02 (s, 2H, CH₂), 4.62 (s, 2H, CH₂), 4.68 (q, 1H, CH), 6.76 (d, 2H, Ar), 7.30 (m, 5H, Ar), 7.42 (d, 2H, Ar), 8.18 (s, 1H, NH)

Example 69

2-[4-(2-Hydroxyacetylamino)phenoxy]propionic acid methyl ester (69)

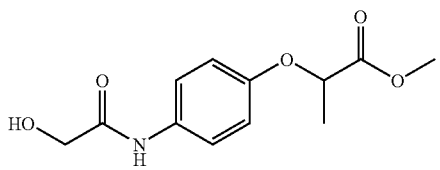

2-[4-(2-Benzyloxyacetylamino)phenoxy]propionic acid methyl ester 68 (15 grams, 43.7 mmol) was dissolved in methanol (150 ml) in a pressure vessel, palladium on carbon (5%, 8 g) added and the mixture stirred under a hydrogen atmosphere (2.5 Kg) for 10 hrs. The catalyst was removed by filtration and the methanol distilled off. The crude 69 was recrystallised in chloroform:hexane (1:6) to give pure 69 (4 g, 36.3%) as a white powder. M.p: 111-112.6° C.

¹H NMR (CDCl₃) δ 1.60 (d, 3H, CH₃), 3.44 (bt, 1H, OH), 3.78 (s, 3H, ester), 4.14 (d, 1H, CH₂OH), 4.72 (q, 1H, CH), 6.80 (d, 2H, Ar), 7.44 (d, 2H, Ar), 8.30 (s, 1H, NH)

Example 70

6-[4-(2-Benzyloxyacetylamino)phenoxy]hexanoic acid methyl ester (70)

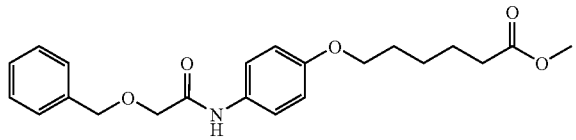

Benzyloxyacetyl chloride (25 gm, 135.5 mmol) was added dropwise to a mixture of 6-(4-aminophenoxy)hexanoic acid methyl ester 21 (25 g, 105 mmol) and triethylamine (21.4 g, 211.6 mmol) in acetone (200 ml) at 0° C. and stirred at room temp. for 12 hrs. Solids were filtered off, acetone distilled off and water (100 ml) added. Crude 70 was extracted into chloroform, washed with 5% sodium bicarbonate solution (2×100 ml), water (100 ml), dried over sodium sulphate and distilled. Crude 70 was purified by column chromatography on silica gel using benzene as eluant to get pure 70 (9 g, 22.2%) as a off-white powder. M.p: 46-49° C.

$^1$H NMR (CDCl$_3$) δ 1.52 (m, 2H, CH$_2$), 1.72 (m, 4H, CH$_2$X2), 2.32 (t, 2H, CH$_2$), 3.68 (s, 3H, ester), 3.92 (t, 2H, CH$_2$), 4.10 (s, 2H, CH$_2$), 4.68 (s, 2H, CH$_2$), 6.82 (d, 2H, Ar), 8.20 (s, 1H, NH)

Example 71

6-[4-(2-Hydroxyacetylamino)phenoxy]hexanoic acid methyl ester (71)

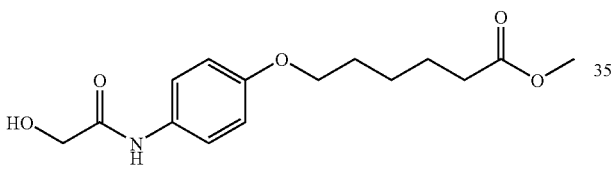

6-[4-(2-Benzyloxyacetylamino)phenoxy]hexanoic acid methyl ester 70(1 g, 2.6 mmol) was dissolved in methanol (10 ml) in a pressure vessel, pd on carbon (5%, 250 mg) added and the mixture stirred under a hydrogen atm. (2 Kg) for 5 hrs. Catalyst was removed by filtration and methanol was distilled off. Crude 71 was recrystallised in chloroform:hexane(1:6) to get pure 71(0.5 g, 65.3%) as a white powder. M.p: 91.5-94° C.

$^1$H NMR (CDCl$_3$) δ 1.45 (m, 2H, CH$_2$), 1.62 (m, 4H, CH$_2$×2), 2.36 (t, 2H, CH$_2$), 3.02 (t, 2H, CH$_2$), 3.02 (t, 1H, OH), 3.68 (s, 3H, ester), 3.92 (t, 2H, CH$_2$), 4.22 (d, 2H, CH$_2$), 6.84 (d, 2H, Ar), 7.46 (d, 2H, Ar), 8.24 (bs, 1H, NH)

Example 72

4-(2-Hydroxyacetylamino)phenoxyacetic acid methoxycarbonyl methyl ester (72)

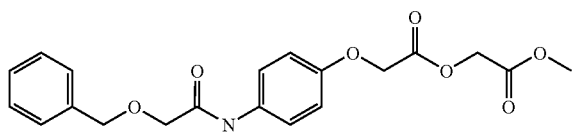

Benzyloxyacetyl chloride (5.8 grs, 31.4 mmol) was added drop-wise to a mixture of 4-aminophenoxyacetic acid methoxycarbonyl methyl ester 62 (5 g, 20.9 mmol) and triethylamine (8.8 ml, 63.1 mmol) in acetone (50 ml) at 0° C. and stirred at room temp. for 20 hrs. The solids were filtered off, acetone distilled off and water (50 ml) added. Crude 72 was extracted into chloroform, washed with 5% sodium bicarbonate (2×50 ml), washed with water (2×50 ml), dried over sodium sulphate and distilled. Crude 72 was purified by column chromatography on silica gel using chloroform as eluant to get pure 72 (5 g, 61.7%) as a light brown powder. M.p: 66.5-69.5° C.

$^1$H NMR (CDCl$_3$) δ 3.78(s, 3H, ester), 4.06 (s, 2H, CH$_2$), 4.64 (s, 2H, CH$_2$), 4.70 (s, 4H, CH$_2$×2), 6.86 (d, 2H, Ar), 7.34 (m, 5H, Ar), 7.48 (d, 2H, Ar), 8.18 (bs, 1H, NH)

Example 73

4-(2-Hydroxyacetylamino)phenoxyacetic acid methoxycarbonyl methyl ester (73)

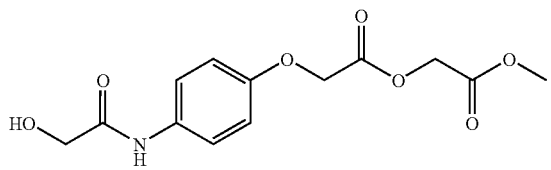

4-(2-Hydroxyacetylamino)phenoxyacetic acid methoxycarbonyl methyl ester 72 (2 g) was dissolved in methanol (20 ml) in a pressure vessel, palladium on carbon (5%, 1 g) added and the mixture stirred under a hydrogen atm. (2.5 Kg) for 10 hrs. Catalyst was removed by filtration and the methanol distilled off. Crude 73 was purified by column chromatography on silica gel using chloroform as eluant to give pure 73 (0.5 g, 32.5%) as a white powder. M.p: 92-95° C.

$^1$H NMR (CDCl$_3$+DMSO, d$_6$) δ 3.75 (s, 3H, ester), 3.88 (d, 2H, CH$_2$OH), 4.74 (s, 2H, CH$_2$), 4.78 (s, 2H, CH$_2$), 5.50 (t, 1H, OH), 6.84 (d, 2H, Ar), 7.58 (d, 2H, Ar), 9.02 (s, 1H, NH)

Example 74

Benzyloxyacetic acid-4-(2-benzyloxyacetylamino)phenyl ester (74)

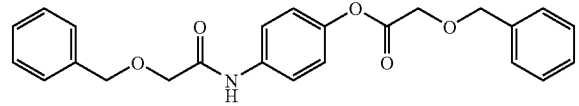

Benzyloxyacetyl chloride (100 gm, 542 mmol) was added drop-wise to a mixture of 4-aminophenol (20 g, 183.26 mmol) and triethylamine (90 g, 889.41 mmol) in acetone (400 ml) at 0° C. and stirred at room temp. for 18 hrs. Solids were filtered off, acetone distilled off and water (200 ml) added. Crude 74 was extracted into chloroform, washed with 5% sodium bicarbonate (2×100 ml), dried over sodium sulphate and distilled. Crude 74 was purified by column chromatography on silica gel using benzene as eluant to give pure 74 (27 g, 36.37%) as light brown powder. M.p: 55.5-58.5° C.

$^1$HNMR (CDCl$_3$) δ 4.02 (s, 2H, OCH$_2$), 4.28 (s, 2H, OCH$_2$), 4.60 (s, 2H, OCH$_2$), 4.70 (s, 2H, OCH$_2$), 7.02 (d, 2H, Ar), 7.32 (m, 10H, Ar), 7.56 (d, 2H, Ar), 8.32 (s, 1H, NH)

Example 75

Hydroxyacetic acid, 4-(2-hydroxyacetylamino)phenyl ester (75)

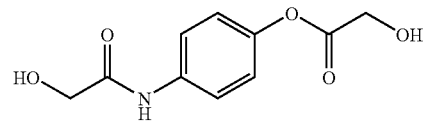

Benzyloxyacetic acid-4-(2-benzyloxyacetylamino)phenyl ester 74 was dissolved in methanol (50 ml) in a pressure vessel, palladium on carbon (5%, 4 grams) added and the mixture stirred under a hydrogen atm. (4 Kg) for 10 hrs. Catalyst was removed by filtration and methanol distilled off under vacuum. Crude 75 was purified by column chromatography on silica gel using benzene:ethyl acetate (8:2) as eluant.

Example 76

4-(6-Benzyloxyhexanoylamino)phenoxyacetic acid methyl ester

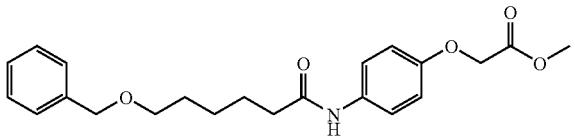

A solution of 1,2-dicyclohexylcarbodiimide (80 g, 387.73 mmol) in anhydrous dichloromethane (100 ml) was added dropwise to a mixture of (4-aminophenoxy) acetic acid methyl ester 15 (20 gm, 110.5 mmol) and benzyloxyhexanoic acid (50 gm, 225.22 mmol) in anhydrous dichloromethane (300 ml) at 0° C. under nitrogen atm. and stirred at room temp. for 16 hrs. The solids were filtered off, and the dichloromethane phase was washed with 5% sodium bicarbonate solution (2×100 ml), with water (2×100 ml), dried over sodium sulphate, and distilled to get crude 76. Crude 76 was purified by column chromatography on silica gel using chloroform as eluant to give 24 g of 4-(6-benzyloxyhexanoylamino)phenoxyacetic acid methyl ester which was further purified by recrystallizing in chloroform:hexane (1:6) to give pure 76 (20 g, 47%) as a white powder. M.p: 64.6-67° C.
$^1$H NMR (CDCl$_3$) δ 1.48 (m, 2H, CH$_2$), 1.68 (m, 4H, CH$_2$), 2.30 (t, 2H, CH$_2$), 3.44 (t, 2H, CH$_2$), 3.78 (s, 3H, ester), 4.44 (s, 2H, CH$_2$), 4.56 (s, 2H, CH$_2$), 6.74 (d, 2H, Ar), 7.30 (m, 5H, Ar), 7.35 (d, 2H, Ar), 7.50 (s, 1H, NH)

Example 77

4-(6-Hydroxyhexanoylamino)phenoxyacetic acid methyl ester (77)

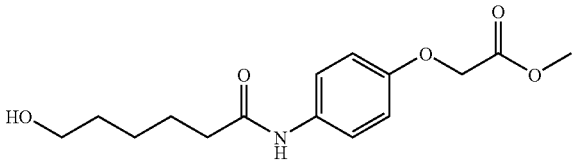

4-(6-Benzyloxyhexanoylamino)phenoxyacetic acid methyl ester 76 (24 grams, 62.33 mmol) was dissolved in a mixture of methanol (200 ml) and dimethylformamide (50 ml) in a pressure vessel, palladium on carbon (5%, 15 g) was added and the mixture stirred under a hydrogen atm. (4 Kg) for 24 hrs. Catalyst was removed by filtration, and the solvents were distilled off under vacuum. Crude 77 was purified by column chromatography on silica gel using chloroform as eluant to get pure 77 (4.5 g, 24.4%) as a white powder. M.p: 87.5-90.4° C.
$^1$H NMR (CDCl$_3$+DMSO-d$_6$) δ 1.40 (m, 4H, CH$_2$), 1.60 (m, 2H, CH$_2$), 2.20 (t, 2H, CH$_2$), 3.40 (t, 2H, CH$_2$), 3.68 (s, 3H, ester), 3.94 (bs, 1H, OH), 4.50 (s, 2H, CH$_2$), 6.68 (d, 2H, Ar), 7.42 (d, 2H, Ar), 9.30 (s, 1H, NH)

Example 78

2-[4-(6-Benzyloxyhexanoylamino)phenoxy]propionic acid methyl ester (78)

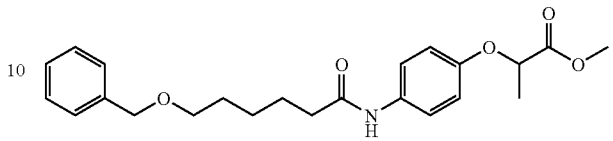

A solution of 1,3-dicyclohexyocarbodiimide (74 g, 358.64 mmol) in anhydrous dichloromethane (75 ml) was added dropwise to a mixture of 2-(4-aminophenoxy) propionic acid methyl ester 18 (20 g, 102.44 mmol) and benzyloxyhexanoic acid (57 g, 256.43 mmol) in anhydrous dichloromethane (250 ml) at 0° C. under nitrogen atm. The reaction mixture was stirred at room temperature for 20 hrs. The solids were filtered off, the dichloromethane phase was washed with 5% sodium bicarbonate (2×100 ml), with water (2×100 ml), dried over sodium sulphate, and distilled to get crude 78. Crude 78 was purified by column chromatography on silica gel using chloroform as eluant to get pure 78 (15 g, 36.7%) as a light pink powder. M.p: 73-76.5° C.
$^1$H NMR (CDCl$_3$) δ 1.45 (m, 2H, CH$_2$), 1.60 (d, 3H, CH$_3$), 1.70 (m, 4H, CH$_2$), 2.45 (t, 2H, CH$_2$), 3.45 (t, 2H, CH$_2$), 3.72 (s, 3H, ester), 4.46 (s, 2H, CH$_2$), 4.66 (q, 1H, CH), 6.70 (d, 2H, Ar), 7.24 (m, 5H, Ar), 7.30 (d, 2H, Ar), 7.54 (s, 1H, NH)

Example 79

2-[4-(6-Hydroxyhexanoylamino)phenoxy]propionic acid methyl ester (79)

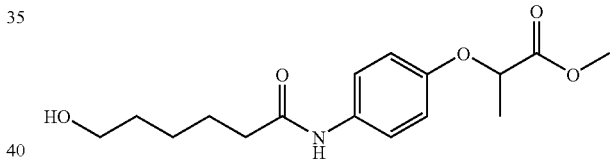

2-[4-(6-Benzyloxyhexanoylamino)phenoxy]propionic acid methyl ester 78 (15 g, 37.59 mmol) was dissolved in methanol (150 ml) in a pressure vessel, palladium on carbon (50% wet, 5%, 15 g) added and the mixture stirred under a hydrogen atmosph. (4 Kg) for 16 hrs. Catalyst was removed by filtration and methanol distilled off. The crude 79 was purified by column chromatography on silica gel using chloroform as eluant to get pure 79 (6 g, 51.6%) as a white powder. M.p: 62-64.5° C.
$^1$H NMR (CDCl$_3$) δ 1.40 (m, 6H, CH$_2$), 1.54 (d, 3H, CH$_3$), 2.21 (t, 2H, CH$_2$), 3.48 (t, 2H, CH$_2$), 3.70 (s, 3H, ester), 4.66 (q, 1H, CH), 6.68 (d, 2H, Ar), 7.36 (d, 2H, Ar), 8.66 (s, 1H, NH)

Example 80

6-[4-(6-Benzyloxyhexanoylamino)phenoxy]hexanoic acid methyl ester (80)

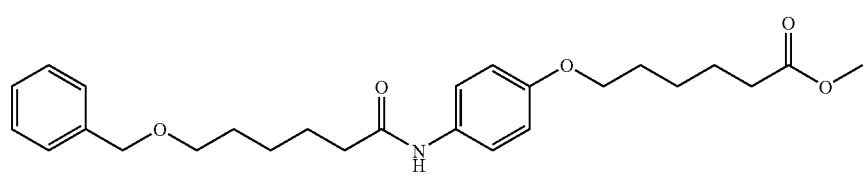

1,3-dicyclohexylcarbodiimide (55 gm, 266.56 mmol) in anhydrous dichloromethane (60 ml) was added dropwise to a mixture of 6-(4-aminophenoxy)hexanoic acid methyl ester 21 (25 g, 105.48 mmol) and benzyloxyhexanoic acid (37.5 g, 168.7 mmol) in anhydrous dichloromethane (250 ml) at 0° C. under nitrogen atm. The reaction mixture was stirred at room temp. for 16 hrs. The solids were filtered off and the dichloromethane phase was washed with 5% sodium bicarbonate solution (2×100 ml), with water (2×100 ml), dried over sodium sulphate and distilled to get crude 80. Crude 80 was purified by column chromatography on silica gel using benzene:hexane (1:1) to get pure 80 (28 g, 60.2%) as a white powder. M.p: 64-65.6° C.

$^1$H NMR (CDCl$_3$) δ 1.48 (m, 2H, CH$_2$), 1.70 (m, 10H, CH$_2$), 2.30 (m, 2H, CH$_2$), 3.48 (t, 2H, CH$_2$), 3.68 (s, 3H, ester), 3.88 (t, 2H, CH$_2$), 4.44 (s, 2H, CH$_2$), 6.72 (d, 2H, Ar), 7.30 (m, 8H, Ar &NH)

Example 81

6-[4-(6-Hydroxyhexanoylamino)phenoxy]hexanoic acid methyl ester (81)

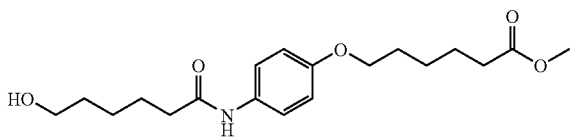

6-[4-(6-Benzyloxyhexanoylamino)phenoxy]hexanoic acid methyl ester 80 (10 g, 22.67 mmol) was dissolved in methanol (100 ml) in a pressure vessel, palladium on carbon (5%, 6 grams) added, and the mixture stirred under a hydrogen atm. (4 Kg) for 20 hrs. Catalyst was removed by filtration and methanol distilled off. Crude 81 was purified by column chromatography on silica gel using chloroform as eluant to give pure 81 (5 g, 62.8%) as a white powder. M.p: 73-75.5° C.

$^1$H NMR (CDCl$_3$) δ 1.40 to 1.80 (m, 12H, CH$_2$), 2.36 (m, 4H, CH$_2$), 3.58 (t, 2H, CH$_2$), 3.64(s, 3H, ester), 3.88(t, 2H, CH$_2$), 6.72(d, 2H, Ar), 7.26(d, 2H, Ar), 7.40(s, 1H, NH)

Example 82

4-(6-Benzyloxyhexanoylamino)phenoxyacetic acid methoxycarbonyl methyl ester (82)

A solution of 1,3-dicyclohexylcarbodiimide (39 g, 189 mmol) was added dropwise to a mixture of (4-aminophenoxy)acetic acid methoxycarbonyl methyl ester 60 (15 g, 62.76 mmol) and benzyloxyhexanoic acid (21 g, 94.47 mmol), in anhydrous dichloromethane (300 ml) at 0° C. under nitrogen atm. The reaction mixture was stirred at room temp. for 18 hrs, the solids were filtered off and the dichloromethane phase was washed with 5% sodium bicarbonate solution (2×75 ml), with water (2×75 ml), dried over sodium sulphate and distilled to give crude 82. Crude 82 was purified by column chromatography on silica gel using chloroform as eluant to get pure 82 (15 g, 53.9%) as a white powder. M.p: 71-73° C.

$^1$H NMR (CDCl$_3$) δ 1.44 (m, 2H, CH$_2$), 1.66 (m, 4H, CH$_2$), 2.30 (t, 2H, CH$_2$), 3.44 (t, 2H, CH$_2$), 3.74 (s, 3H, ester), 4.48 (s, 2H, CH$_2$), 4.70 (s, 4H, CH$_2$), 6.80 (d, 2H, Ar), 7.30 (m, 8H, Ar &NH)

Example 83

4-(6-Hydroxyhexanoylamino)phenoxyacetic acid methoxycarbonyl methyl ester (83)

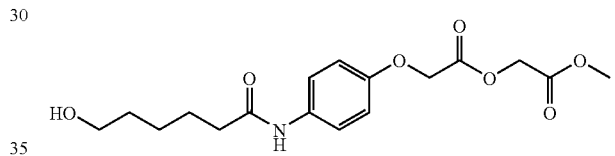

4-(6-Benzyloxyhexanoylamino)phenoxyacetic acid methoxycarbonyl methyl ester 82 (13 g, 29.34 mmol) was dissolved in dimethylformamide (100 ml) in a pressure vessel, palladium on carbon (5%, 10 g) added and the mixture stirred under a hydrogen atm. (4 Kg) for 20 hrs. Catalyst was removed by filtration and dimethylformamide distilled off under vacuum. Ice water (100 ml) was added and the mixture extracted with chloroform, dried over sodium sulphate and distilled to give crude 83. Crude 83 was purified by column chromatography on silica gel using chloroform as eluant to give 6 g of solid, which was further purified by recrystallizing in chloroform:hexane (1:6) to get pure 83 (4 g, 38.6%) as a light pink powder. M.p: 68-70.5° C.

$^1$H NMR (CDCl$_3$) δ 1.44 (m, 2H, CH$_2$), 1.58 (m, 2H, CH$_2$), 1.74 (m, 2H, CH$_2$), 2.30 (t, 2H, CH$_2$), 2.38 (bs, 1H, OH), 3.56 (t, 2H, CH$_2$), 3.78 (s, 3H, ester), 4.70 (s, 4H, CH$_2$), 6.80 (d, 2H, Ar), 7.48 (d, 2H, Ar), 8.74 (s, 1H, NH)

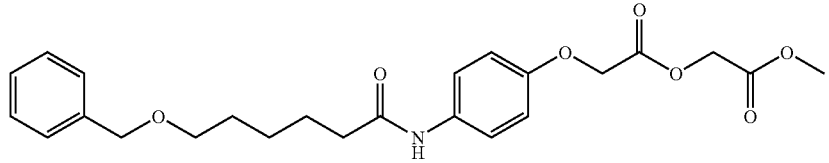

Examples 84-90

Hydrolysis Studies

| Compound | 500 mg |
|---|---|
| Aldrich pH 7.4 Buffer | 50 ml |
| Temperature | 100° C. |
| Method of Study | Thin layer chromatography |

Compound 62 hydrolysed as follows in three hours:

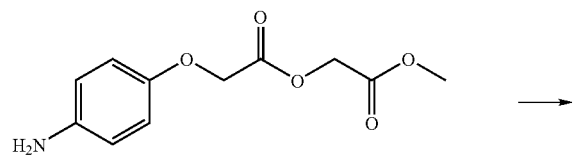

-continued

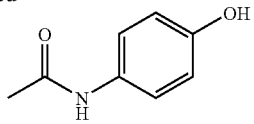

Compound 65 hydrolysed as follows in eight hours:

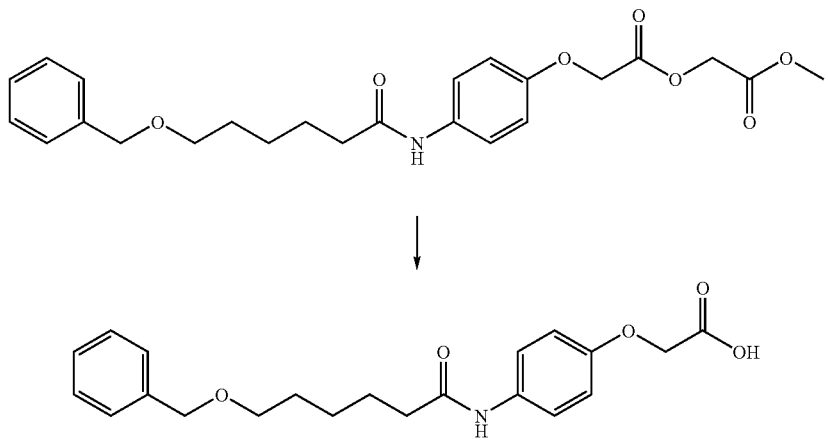

Compound 82 hydrolysed as follows in three hours:

-continued

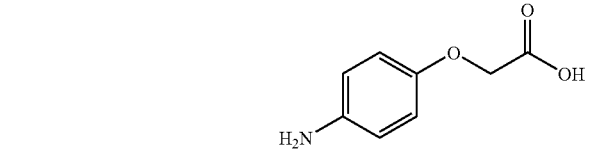

Compound 24 hydrolysed as follows in 1.5 hours:

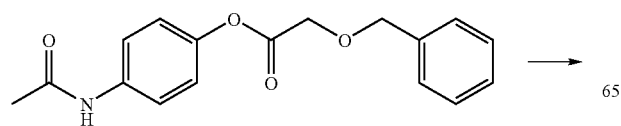

Compound 43 hydrolysed as follows in 11.5 hours:

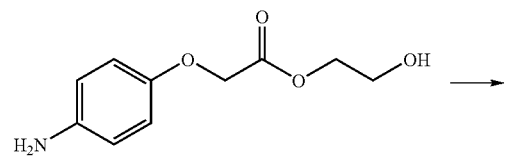

-continued

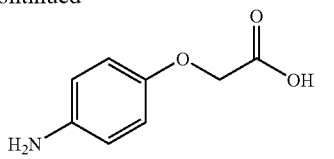

Compound 50 hydrolysed as follows in 40 hours:

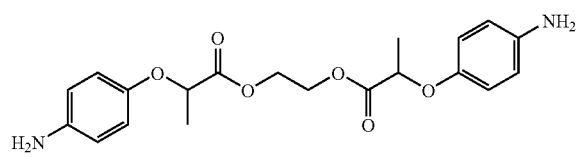

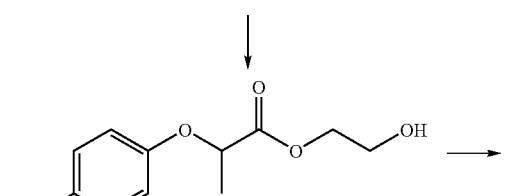

Compound 66 hydrolysed as follows in five hours:

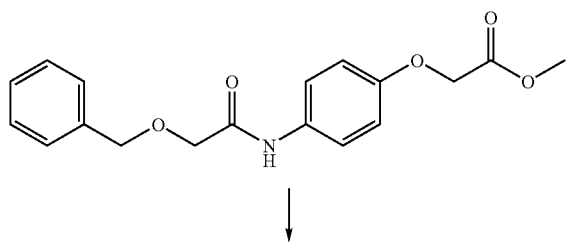

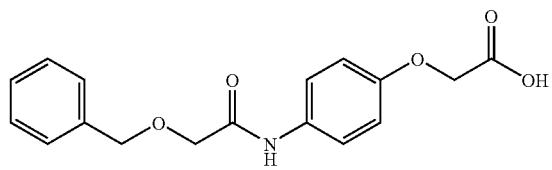

Example 91

2-Carboxymethoxy-benzoic acid (91)

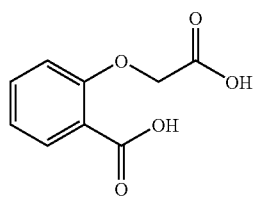

2-Methoxycarbonylmethoxybenzoic acid methyl ester 1 (95 g, 424 mmol) was added to a 10% aqueous NaOH solution (475 ml) and heated at 80° C. for 4 hrs. The reaction mixture was cooled to room temperature and pH adjusted to 2 with dilute HCl. Crude 91 was purified by dissolving in 10% aqueous NaOH and precipitated by acidifying with HCl, to get pure 91 (65 g, 78.2%) as a white powder. M.p: 189-192° C.

Example 92

2-Methoxycarbonylmethoxycarbonylmethoxybenzoic acid methoxycarbonylmethyl ester (92)

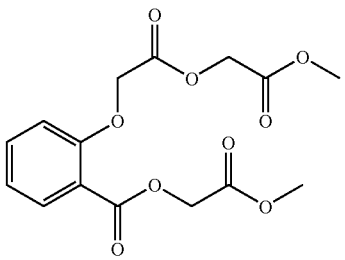

Methylchloroacetate (39 g, 359 mmol) was added dropwise to a mixture of 2-carboxymethoxybenzoic acid 91 (34 g, 173.5 mmol) and triethylamine (37 g, 365.6 mmol) in acetone (100 ml) and stirred under reflux for 24 hrs. Solids were filtered off, acetone distilled off and cold water (150 ml) added. Crude 92 was extracted into chloroform, washed with 5% Sodium bicarbonate (2×100 ml), with water (2×100 ml), dried over sodium sulphate and distilled. Crude 92 was purified by column chromatography on silica gel using hexane as eluant to get pure 92 (31 g, 52.5%) as a light yellow syrup.

Example 93

2-Methoxycarbonylmethoxy-benzoic acid methoxycarbonylmethyl ester (93)

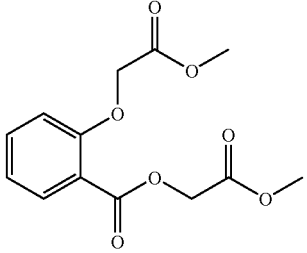

Methylchloroacetate (9.4 g, 86.66 mmol) was added dropwise to a mixture of salicylic acid (10 g, 72.46 mmol) and triethylamine (8.8 g, 86.96 mmol) in acetone (50 ml) and heated to reflux for 10 hrs. Solids were filtered off and potassium carbonate (25 g, 180.89 mmol) was added to the acetone layer together with sodium iodide (2 gm, 13.34 mmol), disodium phosphate (2 g, 14.16 mmol) and methylchloroacetate (9.4 g, 86.66 mmol) and refluxed for 16 hrs. Acetone was distilled off and water (125 ml) added. Crude 93 was extracted into chloroform, washed with 5% sodium bicarbonate solution (2×50 ml), with water (2×50 ml), dried over sodium sulphate and distilled. Crude 93 was purified by column chromatography on silica gel using benzene to get pure 93 (12 g, 58.7%) as a syrup.

Example 94

—Hydrolysis Study

| Compound | 500 mg |
|---|---|
| Aldrich pH 7.4 Buffer | 50 ml |
| Temperature | 100° C. |
| Method of Study | Thin layer chromatography |

Compound 93 hydrolysed as follows in eight hours:

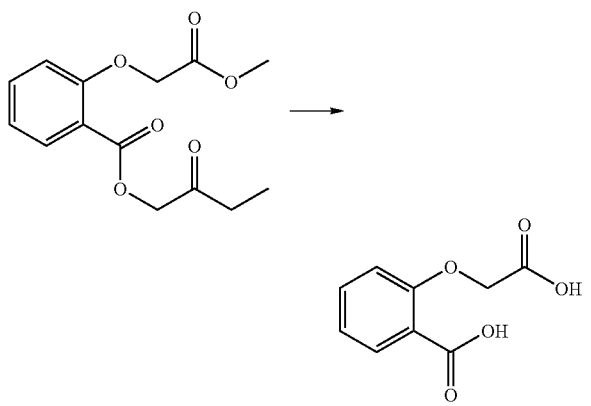

Example 95

2-(6-Methoxycarbonylmethoxycarbonylmethoxynaphthalen-2-yl)-propionic acid methoxycarbonylmethyl ester (95)

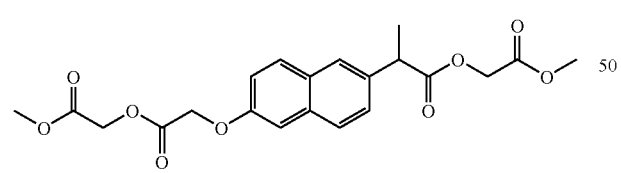

Methyl chloro acetone (22.2 gms, 200.1 mmol) was added drop-wise to a mixture of 2-(6-Carboxymethoxynaphthalen-2-yl)propionic acid 5 (18 gms, 65.69 mmol) Triethyl amine (20.25 gms, 200.1 mmol) in acetone (180 ml) was added Methyl chloro acetone (22.2 gms, 204.5 mmol) drop wise, later heated to reflux for 21 hrs. Solids were filtered off, acetone distilled and water (100 ml) was added. Crude 5 was extracted into chloroform, washed with 5% sodium bicarbonate (2×50 ml), water (2×50 ml), dried over sodium sulphate and distilled. The crude 5 was purified by column chromatography on silica gel using Benzene as elvant to give pure 5 (21 gms, 76.5%) as a light yellow syrup.

$^1$HNMR(CDCl$_3$) δ 1.60(d,3H,CH$_3$), 3.68(s,3H,Ester), 3.74(s,3H,Ester), 3.92(q,1H,CH), 4.55(dd,2H,CH$_2$), 4.70(s, 2H,CH$_2$), 4.80(s,2H,CH$_2$), 7.08(d,1H, Ar), 7.18(m,1H,Ar), 7.30(s,1H,Ar), 7.40(m,1H,Ar), 7.68(m,2H,Ar)

Example 96

2-(6-Carboxymethoxynaphthalen-2-yl)propionic acid (96)

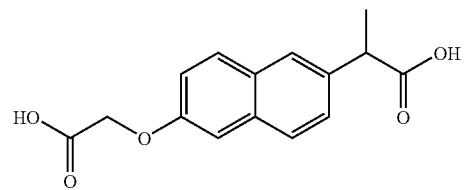

2-(6-Methoxycarbonylmethoxynaphthalen-2-yl)propionic acid methyl ester 7 (23 g, 76.16 mmol) in 4 N aqueous NaOH (230 ml) was heated on a water bath at 90° C. for 8 hrs. The reaction mass was cooled to room temp. and the pH adjusted to 2 with con. HCl. Crude 96 was filtered, dried and recrystallised from a mixture of ethyl acetate:hexane (1:6) to give pure 96 (15 g, 71.9%) as a white powder. Mp: 185-188° C.

$^1$H NMR (DMSO-d$_6$) δ 1.54 (d, 3H, CH$_3$), 3.80 (q, 1H, CH), 4.74 (s, 2H, OCH$_2$), 7.08 (s, 1H, AR), 7.22 (m, 1H, Ar), 7.42 (m, 1H, Ar), 7.66 (m, 3H, Ar)

Example 97

2-(6-Methoxycarbonylmethoxycarbonylmethoxynaphthalen-2-yl)-propionic acid methoxycarbonylmethyl ester (97)

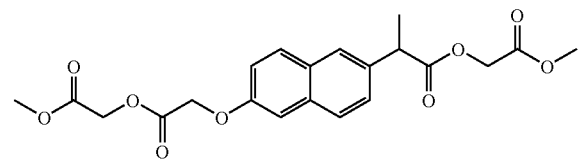

Methyl chloro acetone (22.2 gms, 204.5 mmol) was added drop-wise to a mixture of 2-(6-Carboxymethoxynaphthalen-2-yl)propionic acid 96 (18 g, 65.69 mmol) and triethylamine (20.25 g, 200.1 mmol) in acetone (180 ml) and refluxed for 21 hrs. Solids were filtered off, acetone distilled off and water (100 ml) added. Crude 97 was extracted into chloroform, washed with 5% sodium bicarbonate (2×50 ml), with water (2×50 ml), dried over sodium sulphate and distilled. Crude 97 was purified by column chromatography on silica gel using benzene as eluant to give pure 97 (21 g, 76.5%) as a light yellow syrup.

$^1$HNMR (CDCl$_3$) δ 1.60 (d, 3H, CH$_3$), 3.68 (s, 3H, ester), 3.74 (s,3H, ester), 3.92 (q, 1H, CH), 4.55 (dd, 2H, CH$_2$), 4.70 (s, 2H, CH$_2$), 4.80 (s, 2H, CH$_2$), 7.08 (d, 1H, Ar), 7.18 (m, 1H, Ar), 7.30 (s, 1H, Ar), 7.40 (m, 1H, Ar), 7.68 (m, 2H, Ar)

Example 98

2-(6-Methoxycarbonylmethoxynaphthalen-2-yl)propionic acid methoxycarbonyl methyl ester (98)

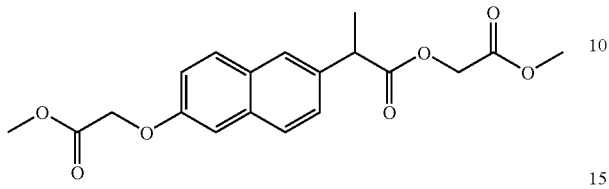

Methyl chloro acetate (13.8 gm, 127.16 mmol) was added drop-wise to a mixture of 2-(6-hydroxynaphthalen-2-yl)propionic acid 5 (25 g, 115.74 mmol) and triethylamine (15.2 g, 150.2 mmol) in acetone (125 ml) and refluxed for 24 hrs. Solids were filtered off and to the acetone layer was added potassium carbonate (30 g, 217 mmol), sodium iodide (4 g, 26.68 mmol), disodium phosphate (4 g, 28.33 mmol) and methylchloroacetate (18 g, 165.86 mmol) and refluxed for 6 hrs. Acetone was distilled off and water (125 ml) added. Crude 98 was extracted into chloroform, washed with 5% sodium bicarbonate solution (2×50 ml), with water (2×50 ml), dried over sodium sulphate and distilled. Crude 98 was purified by column chromatography on silica gel using hexane:ethyl acetate (95:5) to get pure 98 (10 g, 24%) as a light yellow syrup.

$^1$HNMR (CDCl$_3$) δ 1.64 (d, 3H, CH$_3$), 3.72 (s, 3H, Ester), 3.84 (s,3H, ester), 3.95 (q, 1H, CH), 4.58 (dd, 2H, CH$_2$), 4.62 (s, 2H, CH$_2$), 7.04 (d, 1H, Ar), 7.22 (m, 1H, Ar), 7.40 (m, 1H, Ar), 7.70 (m, 3H, Ar)

Example 99

2-[6-(2-Benzyloxyacetoxy)naphthalen-2-yl]propionic acid methyl ester (99)

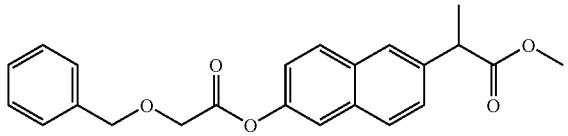

Benzyloxy acetyl chloride (24 gm, 86.95 mmol) was added drop-wise to a mixture of 2-(6-Hydroxynaphthalen-2-yl)-propionic acid methyl ester 6 (20 g, 86.95 mmol) and triethylamine (22.5 g, 222.35 mmol) in acetone (300 ml) and stirred for 2 hrs at room temp. Solids were filtered off, acetone distilled off, and water (100 ml) added. Crude 99 was extracted into chloroform, washed with 5% sodium bicarbonate (2×50 ml), water (2×50 ml), dried over sodium sulphate and distilled. Crude 99 was purified by recrystallising in chloroform:hexane (1:6) to get pure 99 (21 g, 63.9%) as a white powder. M.p: 58-60° C.

$^1$HNMR (CDCl$_3$) δ 1.60 (d, 3H, CH$_3$), 3.68 (s, 3H, ester), 3.86 (q, 1H, CH), 4.38 (s, 2H, CH$_2$), 4.76 (s, 1H, CH$_2$), 7.20 (d, 1H, Ar), 7.36 (m, 5H, Ar), 7.54 (s, 1H, Ar), 7.78 (m, 4H, Ar)

Example 100

2-[6-(2-Hydroxyacetoxy)naphthalen-2-yl]propionic acid methyl ester (100)

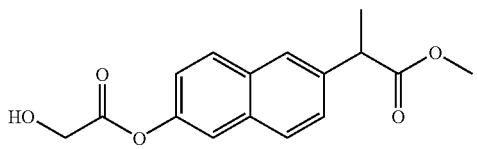

2-[6-(2-Benzyloxyacetoxy) naphthalen-2-yl]propionic acid methyl ester 99 (5 g, 13.22 mmol) was dissolved in ethyl acetate (50 ml) in a pressure vessel, palladium on carbon (5%, 3 g) added and the mixture stirred under a hydrogen atm. (3.5 Kg) for 4 hrs. The catalyst was removed by filtration and ethyl acetate distilled off under vacuum. Hexane was added to precipitate and filtered to give pure 100 (3 g, 78.9%) as off-white powder. M.p: 49.5-52° C.

$^1$HNMR (CDCl$_3$) δ 1.60 (d, 3H, CH$_3$), 3.70 (s, 3H, ester), 3.90 (q, 1H, CH), 4.50 (s, 2H, CH$_2$), 7.22 (dd, 1H, Ar), 7.48 (dd, 1H, Ar), 7.58 (d, 1H, Ar), 7.80 (m, 3H, Ar)

Examples 101-102

Hydrolysis Studies

| Compound | 500 mg |
|---|---|
| Aldrich pH 7.4 Buffer | 50 ml |
| Temperature | 100° C. |
| Method of Study | Thin layer chromatography |

Compound 98 hydrolysed as follows in four hours:

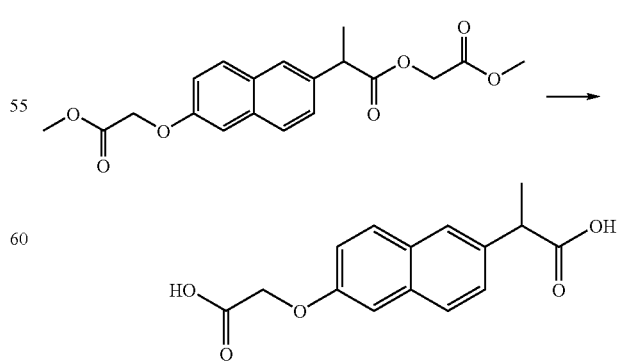

Compound 97 hydrolysed as follows in four hours:

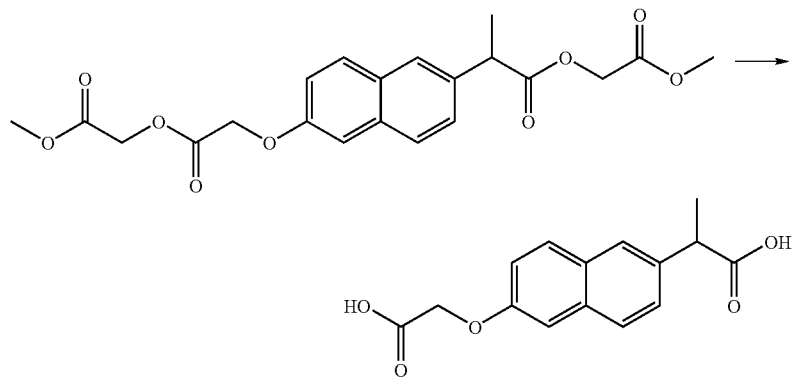

The polymers and oligomers of the present invention can also be used to prepare bioabsorbable chewing gums. After conventional chewing gum is chewed, the gum cud that remains must be discarded. Unfortunately, conventional gum cuds can easily adhere to any dry surface, such as wood, concrete, paper and cloth. When gum cuds are improperly discarded, they can be difficult to remove from such surfaces, causing some environmental concerns. Recently, there has been a move to develop a chewing gum which is either ingestible or that creates a gum cud that is easily removable and degradable. Therefore, this invention also provides hydrolyzable and flexible elastomers that can be used in conventional and specialized biomedical chewing gum. Some of the compositions of this invention can provide improved chewing gum and gum bases. The improved chewing gum and gum bases are biodegradable and do not cause environmental concerns if improperly discarded. The chewing gum and gum bases can also be used as drug delivery systems.

The foregoing examples and description of the preferred embodiments should be taken as illustrating, rather than as limiting, the present invention as defined by the claims. As would be readily appreciated, numerous combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A compound of the formula:

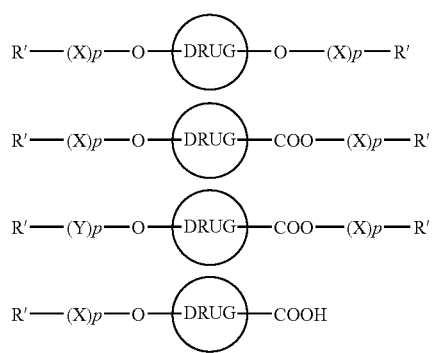

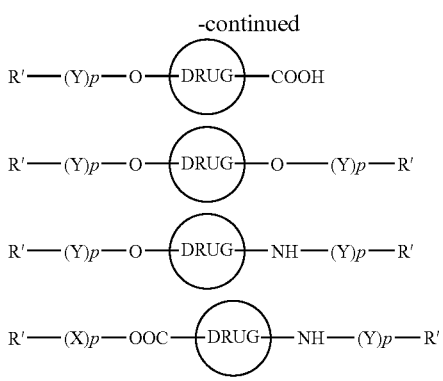

wherein HO-DRUG-OH, HO-DRUG-COOH, HO-DRUG-NH$_2$, and HOOC-DRUG-NH$_2$, are biologically active compounds, and selected from the group consisting of adrenalone, apomorphine, azacyclonol, baclofen, diclofenac, dienestrol, diflunisal, etilefrine, fendosal, flufenamic acid, hexylresorcinol, hydroxyethyl salicylate, ifenprodil, mefenamic acid, naproxen, paracetamol, salicylic acid, salsalate, and tolcapone;

each X represents a member independently selected from the group consisting of:
—CH$_2$COO-(glycolic acid moiety);
—CH(CH$_3$)COO-(lactic acid moiety);
—CH$_2$CH$_2$OCH$_2$COO-(dioxanone moiety);
—CH$_2$CH$_2$CH$_2$CH$_2$CH$_2$COO-(caprolactone moiety);
—(CH$_2$)$_y$COO-where y is one of the numbers 2,3,4 and 6-24 inclusive; and
—(CH$_2$CH$_2$O)$_z$CH$_2$COO-where z is an integer between 2 and 24, inclusive;

each Y represents a member independently selected from the group consisting of:
—COCH$_2$O-(glycolic ester moiety);
—COCH(CH$_3$)O-(lactic ester moiety);
—COCH$_2$OCH$_2$CH$_2$O-(dioxanone ester moiety);
—COCH$_2$CH$_2$CH$_2$CH$_2$CH$_2$O-(caprolactone ester moiety);
—CO(CH$_2$)$_m$O-where m is an integer between 2-4 and 6-24 inclusive; and
—COCH$_2$O(CH$_2$CH$_2$O)$_n$-where n is an integer between 2 and 24, inclusive;

each R' is independently a hydrogen, benzyl or an alkyl group, the alkyl group being either straight-chained or branched, each p is independently an integer between 1 and 6, inclusive;

with the proviso that the resultant compound can only include one $COCH_2O(CH_2CH_2O)_n$ moiety.

2. A compound according to claim 1 wherein each X is independently selected from the group consisting of:
- —$CH_2COO$-(glycolic acid moiety),
- —$CH(CH_3)COO$-(lactic acid moiety),
- —$CH_2CH_2OCH_2COO$-(dioxanone moiety), and
- —$CH_2CH_2CH_2CH_2CH_2 COO$-(caprolactone moiety); and each Y is independently selected from the group consisting of:
- —$COCH_2O$-(glycolic ester moiety);
- —$COCH(CH_3)O$-(lactic ester moiety);
- —$COCH_2OCH_2 CH_2O$-(dioxanone ester moiety); and
- —$COCH_2CH_2CH_2CH_2CH_2O$-(caprolactone ester moiety).

3. A composition comprising two or more different species of the compound according to claim 1.

4. An anti-inflammatory composition comprising an effective amount of at least one compound of claim 1, wherein HO-DRUG-OH, HO-DRUG-COOH, HO-DRUG-$NH_2$, and HOOC-DRUG-$NH_2$ are selected from the group consisting of diclofenac, diflunisal, fendosal, flufenamic acid, hydroxyethyl salicylate, mefenamic acid, naproxen, paracetamol, salicylate acid and salsalate; have a pharmaceutically acceptable excipient; and optionally further comprising a second anti-inflammatory agent.

5. A pain-reducing composition comprising an effective amount of at least one compound of claim 1, wherein HO-DRUG-OH, HO-DRUG-COOH, HO-DRUG-$NH_2$, and HOOC-DRUG-$NH_2$, have pain-reducing properties; a pharmaceutically acceptable excipient; and optionally further comprising a second pain-reducing agent.

6. A bioactive composition comprising an effective amount of at least one compound of claim 1 and a pharmaceutically acceptable excipient, wherein said composition is in a form suitable for oral, enteral, parenteral, topical, transdermal, ocular, vitreal, rectal, nasal, pulmonary, or vaginal administration.

7. A pharmaceutical composition comprising an effective amount of at least one compound of claim 1 and a pharmaceutically acceptable excipient.

8. An antioxidant composition comprising an effective amount of at least one compound of claim 1, where HO-DRUG-OH, HO-DRUG-COOH, HO-DRUG-$NH_2$, and HOOC-DRUG-$NH_2$, have antioxidant properties; a pharmaceutically acceptable excipient; and optionally further comprising a second antioxidant compound.

9. A method for the reduction of pain which comprises administering to a subject in need thereof by means of controlled release drug delivery a therapeutically effective amount of at least one compound of claim 5.

10. A method for the treatment of inflammation which comprises administering to a subject in need thereof by means of controlled drug delivery a therapeutically effective amount of at least one compound of claim 4.

11. A compound according to claim 1 wherein HO-DRUG-OH, HO-DRUG-COOH, HO-DRUG-$NH_2$, and HOOC-DRUG-$NH_2$ are selected from the group consisting of diflunisal, fendosal, hydroxyethyl salicylate, naproxen, paracetamol, salicylic acid, and salsalate.

* * * * *